(12) United States Patent
Numata et al.

(10) Patent No.: US 6,668,036 B2
(45) Date of Patent: Dec. 23, 2003

(54) DATA PROCESSING METHOD AND DATA PROCESSING APPARATUS

(75) Inventors: Shouhei Numata, Hitachi (JP); Tarou Takagi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/347,433

(22) Filed: Jan. 21, 2003

(65) Prior Publication Data

US 2003/0147505 A1 Aug. 7, 2003

Related U.S. Application Data

(63) Continuation-in-part of application No. 10/086,714, filed on Mar. 4, 2002.

(30) Foreign Application Priority Data

Aug. 2, 2001 (JP) .......................................... 2001-234387
Jul. 31, 2002 (JP) .......................................... 2002-222352

(51) Int. Cl.[7] ................................................ A61B 6/03
(52) U.S. Cl. ............................ 378/4; 378/901; 382/131
(58) Field of Search ................................ 378/4, 15, 19, 378/94; 382/131

(56) References Cited

FOREIGN PATENT DOCUMENTS

| JP | 06-202612 | 7/1994 |
| JP | 06-251078 | 9/1994 |

OTHER PUBLICATIONS

Shuudou, Yasuzo, "Three–Dimensional Image Processing in Medical Science", Corona Pub. Co., Ltd., 1995 pp. 55–59.

Primary Examiner—David V. Bruce
(74) Attorney, Agent, or Firm—Mattingly, Stanger & Malur, P.C.

(57) ABSTRACT

A method and an apparatus for processing data enables to display a preview image rapidly in case of processing large volume of data. Index data are generated by rendering the large amount of bit map data and stored in addition to the three-dimensional bit map data. By means that the two-dimensional image resulted from the rendering process is made prepared in advance before accepting the user's command for display and edit, the preview of the content of the data can be displayed rapidly at real-time when the user issues the command interactively.

16 Claims, 20 Drawing Sheets

DATA PROCESSING METHOD AND DATA PROCESSING APPARATUS

CROSS REFERENCE TO THE RELATED APPLICATION

This is a Continuation-in-Part Application of U.S. patent application Ser. No. 10/086,714, filed on Mar. 4, 2002, which is now co-pending.

BACKGROUND OF THE INVENTION

1. Field of the Invention

1. The present invention relates to the data processing method and the data processing apparatus thereof.

2. Description of the Related Art

In case of applying X-ray Computed Tomography (hereinafter referred to as X-ray CT) to non-contact internal dimensional measurement, various kinds of three-dimensional image processing are applied to the three-dimensional bit map data obtained by stacking multi-layered tomographic images defined as two-dimensional bit map data. This technology is used in the medical field, and described in the publication (for example, Three-dimensional image processing in Medical Science by Yasuzo Shuudou, Corona Publishing Co., 1995).

In many cases, for various kinds of data processing for three-dimensional image processing, the following procedures are used. That is, the user supplies commands to the program and the program in response to those commands processes the data (this is called interactive).

In this interactive process, it is required to minimize the user's additional operations due to his or her erroneous operation. For this reason, many programs provides an undo (data and/or operation recovery) function. This function means that the data before processing is stored temporarily, and the data after processing is replaced by the data before processing when the undo command is issued. The user who has noticed his or her erroneous operation can cancel his or her latest operation by inputting the undo command and restart his or her operation from this point. If several sets of data before processing could be stored temporarily, the user can cancel several latest operations backward and restart the operation at any point.

In association with the function described above, Japanese Patent Laid-Open Number 6-251078 (1995) discloses an information processing apparatus in which scale-down image data corresponding to the image data represented as bit map data are arranged and the list of scale-down image data are shown and made selected. Japanese Patent Laid-Open Number 6-202612 (1995) discloses a graphic editor apparatus which provides a display part having a display area for the image edition allowing the user to edit the image and a target object image display area for displaying plural screens of the images in process of edition work.

The prior art described above does not consider the processing of large amount of three-dimensional bit map data over several hundreds megabyte obtained by the high resolution X-ray CT (in this specification, the data having the volume between 100 megabyte and 1 Peta byte is called large amount of data). In many cases, the volume of data is limited below 1P (1 Peta byte) because the technical difficulty occurs in dealing large amount of data.

The volume of the three-dimensional bit map data is proportional to the cubic of the long dimension of the image. A direct application of the apparatus disclosed in Japanese Patent Laid-Open Number 6-251078 (1995) and the conventional method used for three-dimensional bit map operation in the conventional practical field of medical science may arise some problems.

According to the original experiment by the inventors, in case of dealing such large amount of three-dimensional bit map data, it is understood that it takes 10 minutes or longer to display fully the data even by the current computer performance. This is because the image processing called rendering is required to display the three-dimensional bit map data, and it may take an extended time to complete this operation in case that the volume of data is too large. From the user's view, in case of displaying the data in order to confirm the content of the data, such an extended time is required for processing the individual data file in order to browse the content of the individual data.

In case of applying the technology disclosed in Japanese Patent Laid-Open Number 6-251078 (1995) to the three-dimensional bit map data used in the field of medical science, as the time spent in generating the scale-down bit map data from the three-dimensional bit map data (in this case, the volume of data is relatively small) is longer than the time spent for rendering the original three-dimensional bit map data and displaying the resulting image, the time required for confirming the content of the file does not make any significant problem.

In the method for generating the scale-down data of the overall data set later on to be used for search, as disclosed in Japanese Patent Laid-Open Number 6-251078 (1995), there is such a problem that the scale-down operation for the data is required to be done by the user.

In the process of large amount of three-dimensional bit map data, its process itself gives rise to a problem. There may be such a condition that the memory space runs short if the data is stored in the memory every time when the process is repeated. Thus, the number of undo operations (the number of allowable operations to be cancelled) is limited.

In such a method that the rendering operations is performed and the data is displayed every time when the undo command is issued, if the number of undo operations is larger, the fraction of the total waiting time for the user occupied in the overall operation time becomes extremely long because it takes an extended time to be spent for display process.

SUMMARY OF THE INVENTION

An object of the present invention is to provide a data processing method and its processing apparatus enabling to display a preview image rapidly in case of processing large amount of data.

In order to attain the above object, in the present invention, index data are generated by rendering the large amount of bit map data and stored in addition to the three-dimensional bit map data.

It is required to render the large amount of bit map data in order to generate a display image. The rendering process requires an extended period of time. On the contrary, by means that the two-dimensional image resulted from the rendering process is made prepared in advance before accepting the user's command for display and edit, the preview of the content of the data can be displayed rapidly at real-time when the user issues the command interactively.

According to the first aspect of the present invention, a data processing apparatus comprises:

a storage device storing a three-dimensional bit map data and a two-dimensional image data obtained through rendering of the three-dimensional bit map data;

a data processing unit processing the three-dimensional bit map data stored in the storage device, processing a three-dimensional bit map data after process in the storage device, rendering of the three-dimensional bit map data stores in the storage device, and feeding an obtained two-dimensional image data to a display device; and the display device for displaying data fed from the data processing unit.

According to the second aspect of the present invention, a data processing apparatus comprises:

a storage device for storing a three-dimensional bit map data and a scale-down three-dimensional bit map data generated by compressing the three-dimensional bit map data;

a data processing unit processing the scale-down three-dimensional bit map data stored in the storage device, processing a scale-down three-dimensional bit map data after process in the storage device, and feeding obtained scale-down three-dimensional bit map data after the process to a display device; and the display device for displaying data fed from the data processing unit.

According to the third aspect of the present invention, a data processing apparatus comprises:

a storage device for storing a three-dimensional bit map data, a scale-down three-dimensional bit map data generated by compressing the three-dimensional bit map data and a two-dimensional image data obtained through rendering of the scale-down three-dimensional bit map data;

a data processing unit processing the scale-down three-dimensional bit map data stored in the storage device, processing a scale-down three-dimensional bit map data after process in the storage device, rendering of the scale-down three-dimensional bit map data stored in the storage device and feeding obtained two-dimensional image data to a display device; and the display device for displaying data fed from the data processing unit.

The storage device may store at least a part of process history data relating to history of process provided for the scale-down three-dimensional bit map data.

In the preferred construction, a data volume of the three-dimensional bit map data is greater than or equal to 100 Mega bytes and smaller than or equal to 1 Peta bytes.

According to the fourth aspect of the present invention, a data processing method comprises the steps of:

applying a plurality of processes for a three-dimensional bit map data;

rendering of a plurality of three-dimensional bit map data after process; and displaying at least a plurality of obtained two-dimensional image data together on a display device.

The data processing method may further comprise a step of displaying information relating to a history of process applied to the three-dimensional bit map data in association with corresponding two-dimensional image data.

According to the fifth aspect of the present invention, a data processing method comprises the steps of:

deriving a scale-down three-dimensional bit map data by compressing a three-dimensional bit map data;

applying a plurality of processes for the scale-down three-dimensional bit map data; and displaying at least a plurality of scale-down three-dimensional bit map data together on a display device.

According to the sixth aspect of the present invention, a data processing method comprises the step of:

deriving a scale-down three-dimensional bit map data by compressing a three-dimensional bit map data;

applying a plurality of processes for the scale-down three-dimensional bit map data;

rendering for a plurality of scale-down three-dimensional bit map data; and displaying at least a plurality of two-dimensional image data together on a display device.

The data processing method may further comprise a step of displaying information relating to a history of process applied to the scale-down three-dimensional bit map data in association with one of corresponding scale-down three-dimensional bit map data and corresponding the two-dimensional image data.

According to the seventh aspect of the present invention, a data processing method comprises the steps of:

acquiring three-dimensional bit map data by picking-up image of a sample by an X-ray CT apparatus on the basis of a demand of client;

generating at least one of a scale-down three-dimensional bit map data by compressing the three-dimensional bit map data, a two-dimensional bit map data by rendering of the three-dimensional bit map data and a two-dimensional bit map data by compressing the three-dimensional bit map data and rendering for same; and transmitting generated data to the client and transmitting the three-dimensional bit map data corresponding to comment information of the client with respect to the transmitted data.

According to the eighth aspect of the present invention, a data processing method comprises the steps of:

receiving at least one of a scale-down three-dimensional bit map data by compressing the three-dimensional bit map data acquired by picking up an image of sample by means of X-ray CT apparatus, a two-dimensional bit map data by rendering of the three-dimensional bit map data and a two-dimensional bit map data by compressing the three-dimensional bit map data and rendering for same from a service provider;

providing a comment information for the received data to the service provider; and receiving the three-dimensional bit map data corresponding to the comment information from the service provider.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Embodiment 1

An embodiment of processing the three dimensional bit map data is described below.

Figure 20:
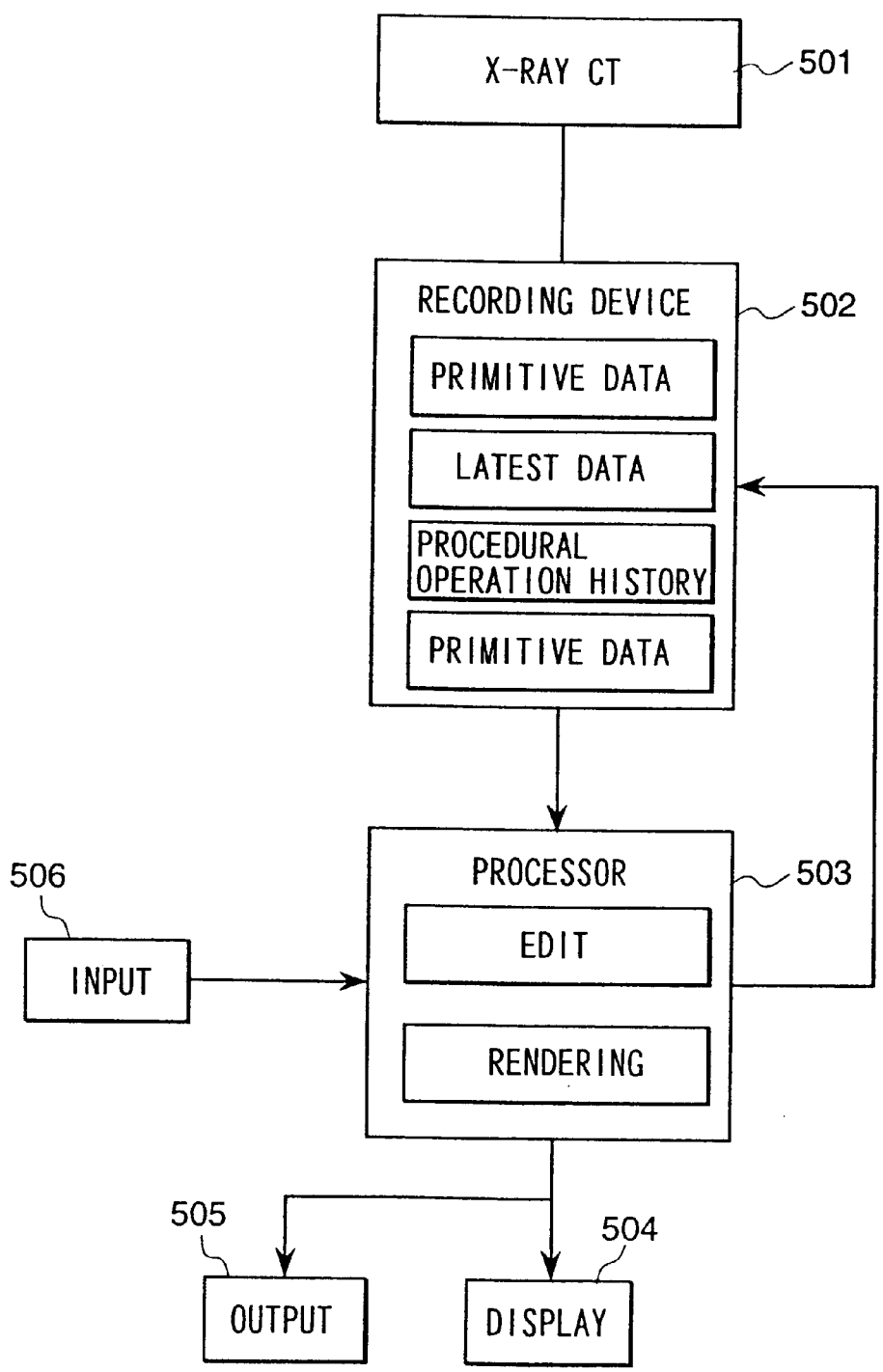
FIG. 20 is a system conceptual diagram.

The outline of the processing apparatus to be used in this embodiment is now described. FIG. 20 shows a conceptual diagram of the processing apparatus. The processing apparatus stores the data taken by the X-ray CT 501 in the storage device 502. The user issues commands to the electronic computer 503 by the input means 506, and specifies various operations. The electronic computer 503 accordingly reads out the necessary data from the memory device 502. The memory device 502 stores the primitive 3DBMD 102, the latest 3DBMD 103, the process history data 105 and the index data 106 to be described later. In response to the commands issued from the input apparatus 506, the electronic computer 503 outputs the data specified by the commands issued by the input apparatus to the output means 505 (printer) and the display device 504 (display). The electronic computer 503 can perform an editing operation for the various data a rendering operation for data (to be described later). The electronic computer 503 can stores the data into the memory device 502 if required. The concept of the overall processing apparatus is so described as above.

Next, the processing apparatus will be described concretely. At first, the image of the target object is captured by the three-dimensional X-ray CT. The target object in this embodiment is assumed to be a metallic turbine for the automobile turbo engines (not shown). The three-dimensional X-ray CT is formed as such an apparatus that the X-ray is irradiated as a fan beam and the image of the target object is captured by detecting the X-ray transmitted through the target object is detected by the sensors. The captured image is stored in the memory device (formed as a hard disk in this embodiment) as the primitive three-dimensional bit map data (hereinafter, three-dimensional bit map data is referred to as 3DBMD).

Figure 4:
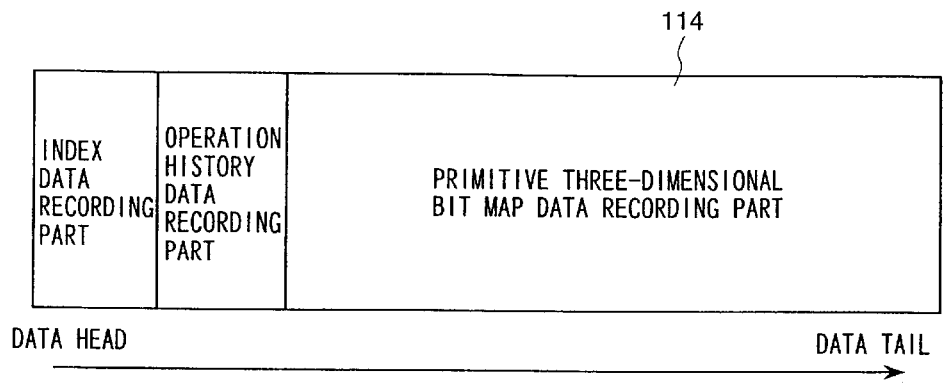
FIG. 4 is an example of three-dimensional bit map data format
Figure 5:
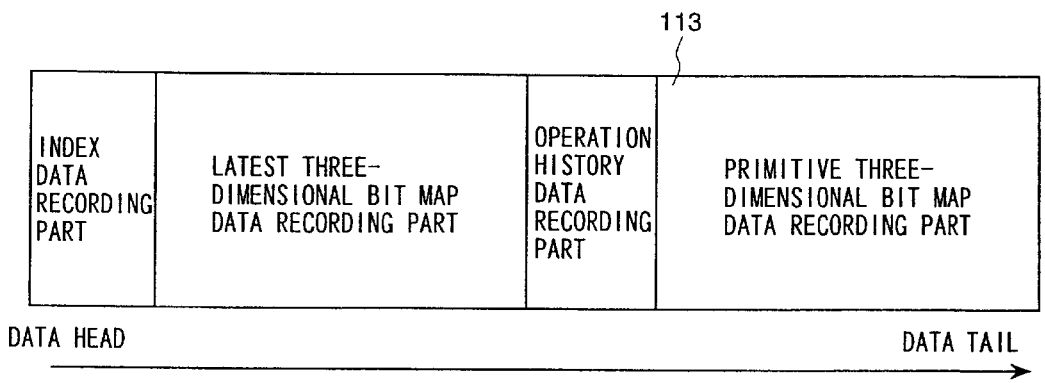
FIG. 5 is an example of three-dimensional bit map data format

Next, the primitive 3DBMD is made converted to the 3DBMD specific to this embodiment. FIG. 4 and FIG. 5 show the formats of the 3DBMD specific to this embodiment.

The header of the 3DBMD 114 with index and procedural operation history shown in FIG. 4 contains the index data recording part and next the procedural operation history data recording part, followed by the recording part for the primitive 3DBMD. The index data represent plural two-dimensional images (or a single image, if allowable) formed by viewing the primitive 3DBMD in a single direction or plural directions. In this embodiment, the data format of the index data is such a format as to be displayed without rendering. In this embodiment, JPEG so-called generally is used for this data format. It is allowed to use GIF so called generally.

The index data is generated by forming the two-dimensional image by viewing the primitive data in a predetermined direction after obtaining the primitive 3DBMD captured by X-ray CT. The formation of the index data is to render the primitive 3DBMD and generate the two-dimensional image. This formation is completed before browsing and processing 3DBMD.

When displaying the index data (two-dimensional image, in this embodiment), the rendering process is not required. The volume of the data is smaller than the volume of the primitive 3DBMD. Thus, the time spent for displaying the index data can be made shorter than the time spent for generating the two-dimensional image from the primitive 3DBMD and displaying the generated image. In addition, by means of generating the index data before hand, the content of the data can be confirmed in a shorter period of time than the two-dimensional data is generated from the 3DBMD every time when the browsing operation is attempted. And furthermore, by means of reading only the index data, it is allowed to refer briefly to the content of the primitive 3DBMD without reading the primitive 3DBMD. For the large volume of 3DBMD, as the volume of its index data is so small, from one per several tens to one per some hundreds of the volume of 3DBMD, the volume of the index data remains unchanged for any case.

In addition, the two-dimensional data obtained by processing the primitive 3DBMD in the process of browsing operations are recorded into the index data.

The procedural operation history data recording part records the history of operations applied to the primitive 3DBMD. In case that the user requires an image to be obtained by processing further the index data corresponding to the state of the processed primitive 3DBMD, the primitive 3DBMD is so processed as to be the state corresponding to the index data, and further processed so as to be the required image.

The primitive 3DBMD with index and procedural operation history 113 shown in FIG. 5 has such a data format that records the primitive 3DBMD concurrently when storing the latest processed 3DBMD. The data format contains a header for the index data and next the latest 3DBMD recording part followed by the procedural operation history data recording part and the primitive 3DBMD recording part. The index data 106 records the rendered image of the latest 3DBMD and the rendered data obtained in the series of procedures from the primitive 3DBMD to the latest 3DBMD as the index data. The procedural operation history data records a series of procedures applied from the primitive 3DBMD to the latest 3DBMD. This means that the application of the series of procedures recorded in the procedural operation history data to the primitive 3DBMD can generate the latest 3DBMD. According to this data format, the outline of the latest 3DBMD can be confirmed briefly at first by displaying the index data. In case of attempting to regenerate the latest 3DBMD (when undo the past processing applied to the latest 3DBMD), the desired 3DBMD to be obtained by applying the undo operation for the past processing can be generated equivalently-by applying the procedural operation history data corresponding to the designated step to the series of past procedures to the primitive 3DBMD by referring to the primitive 3DBMD and the procedural operation history data.

Figure 1:
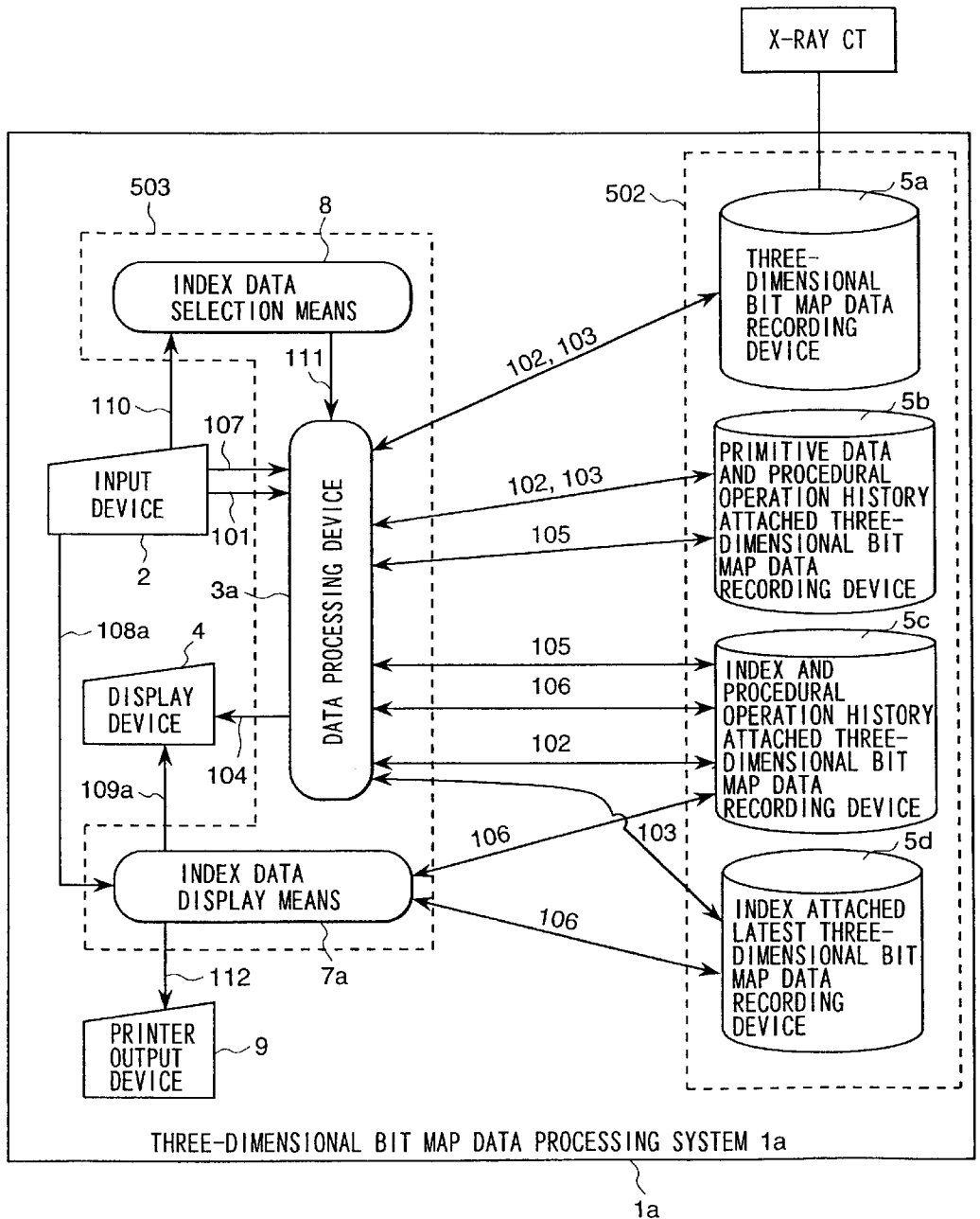
FIG. 1 is a system configuration diagram.

FIG. 1 illustrates a schematic diagram of the 3DBMD processing system 1a using two formats of 3DBMD. This system assumes that the 3DBMD is processed interactively by the user inputting the data processing method (commands) from the input device 2. In this embodiment, the storage device 502 is so configured as to includes individually the 3DBMD recording device 5a, the primitive, index and procedural operation history attached 3DBMD recording device 5b, the index and procedural operation history attached 3DBMD recording device 5c and the index attached the latest 3DBMD 5d, but the storage device 502 may be formed alternatively in another configuration as far as recording those elements of data. The electronic computer 503 is so configured as to include individually the index data selection means 8, the data processing device 3a and the index data display means 7a, each corresponding to their specific tasks, which may be formed as a single computer performing those tasks.

In response to the command input by the user, the input device 2 generates the data processing command 101 and the index data selection command 110. The 3DBMD processing system 1a has a display device 4 for displaying the 3D bit map display image data 104 and the index data display data 109a.

The processing system 1a has the following three recording devices. The 3DBMD recording device 5a records the primitive 3DBMD 102 and the latest 3DBMD. The primitive, index and procedural operation history attached 3DBMD recording device 5b records the primitive, index and procedural operation history attached 3DBMD 113. The index and procedural operation history attached 3DBMD recording device 5c records the index and procedural operation history attached 3DBMD 114. The data processing device 3a can read out the latest 3DBMD 103, the primitive 3DBMD data 102 and the procedural operation history data 105 separately from the primitive, index and procedural operation history attached 3DBMD recording device 5b. The data processing device 3a can read out the index data 106, the procedural operation history data 105 and the primitive 3DBMD 102 separately from the index and procedural operation history attached 3DBMD recording device 5c.

The 3DBMD processing system 1a has the following configuration. The data processing device 3a generates the recording history data 105 and the index data 106 from the primitive 3DBMD 102 and the latest 3DBMD 103. The data processing device 3a also performs various procedures in response to another command. In response to the index data display command 108a, the index data display means 7a generates the index data display data 109a from plural sets of index data 106, and transfers it to the display device 4. In response to the index data selection command 110, the index data selection means 8 generates the reprocessing command 111 and transfer it to the data processing device 3a.

Figure 2:
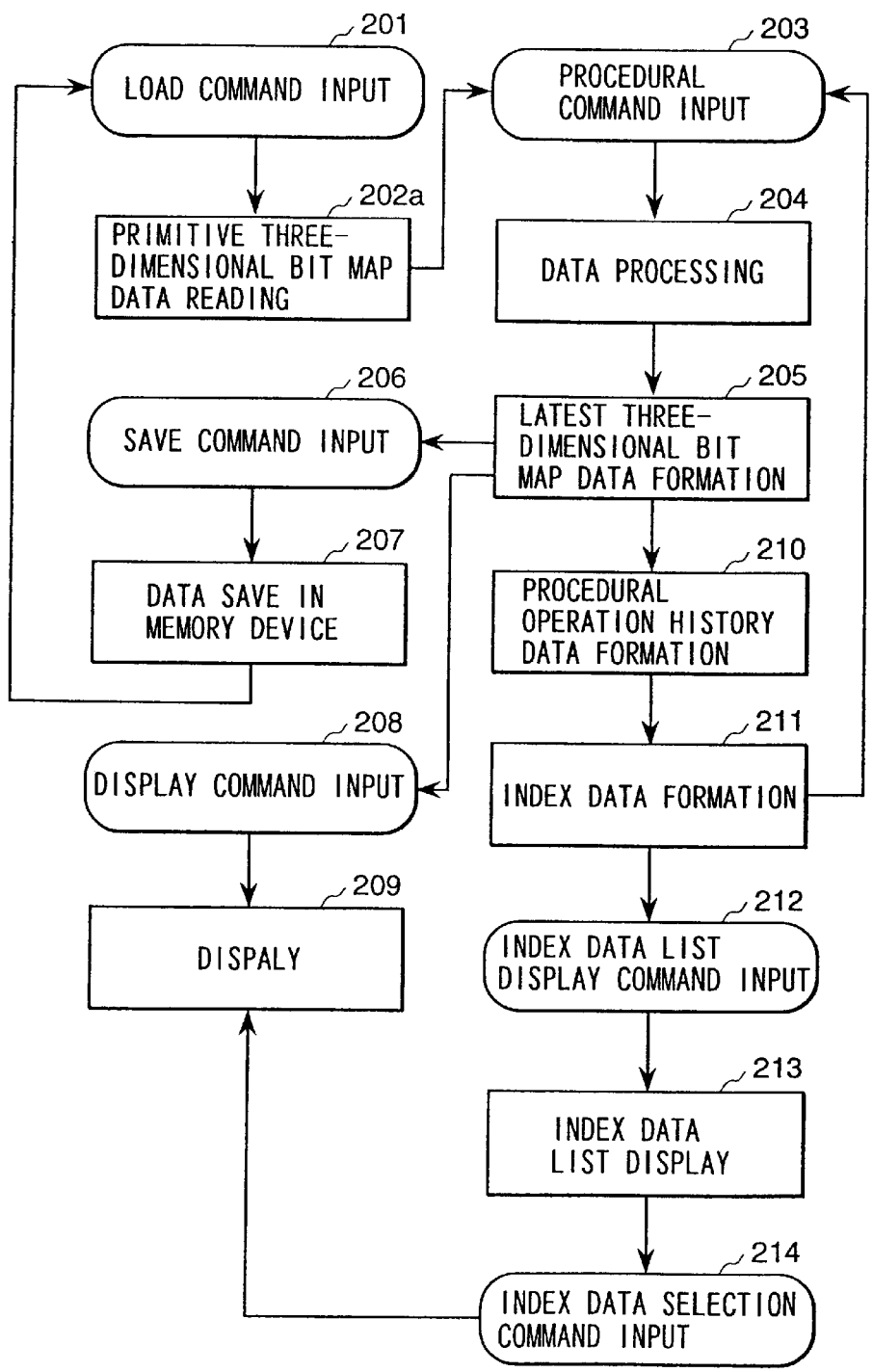
FIG. 2 is a process flowchart.

Next, FIG. 2 illustrates a flowchart for processing the 3DBMD without index data and procedural operation history data in the 3DBMD processing system 1a. This flowchart shows the procedures in which the index data and the procedural operation history data are generated along with processing the 3DBMD in order to speed up the plural sets of procedures (or the procedures in the next phase or later).

The data are exchanged among the individual devices shown in FIG. 1 at the each step of the procedural flow.

At first, the user inputs the load command 201 by using the input device 2. In response to the load command 201, the data processing device 3a reads in the primitive 3DBMD 102 from the 3DBMD recording device 5a (Step 202a). Next, the user inputs the processing command 203 by using the input device 2. The processing command 203 is a command for decomposing the primitive 3DBMD 102 or extracting a part of the primitive 3DBMD 102. In response to the processing command 203, the data processing device 3a applies image processing to the primitive 3DBMD 102 (Step 204), and then generates the latest 3DBMD 103 (Step 205). In case that the user inputs the display command 208 in this step, rendering processing is applied to the latest 3DBMD 103 in order to generate the three-dimensional bit map display image data 104, and then the three-dimensional bit map display image data 104 is transferred to the display device 4 and the latest 3DBMD 103 is displayed (Step 209). According to those procedural commands, the procedural operation history data 105 is generated by the data processing device 3a (Step 210). In addition the data processing device 3a generate the index data from the displayed image (Step 211). The procedural operation history data 105 and the index data 106 generated in the previous steps are stored in the index and procedural operation history attached 3DBMD recording device 5c in the format for the index and procedural operation history attached 3DBMD 114 together with the primitive 3DBMD 102. The procedural steps from the step 203 for accepting the procedural command to the step 211 are repeated for the continuous processing. The index data 106 and the procedural operation history data 105 are updated sequentially in the index and procedural operation history attached 3DBMD recording device 5c.

In case that the user inputs the index data review command 212 with the input device 2, the data processing device 3a displays a list of the stored index data 106 on the display device (Step 213).

Alternately, in case that the user inputs the index data selection command 214 for selecting one of the displayed index data 106, the selected index data 106 is extracted and its magnified view is displayed on the display device 4 (Step 209).

Thus, along with the procedures for applying the image processing to the primitive 3DBMD and generating the latest 3DBMD 103, the procedural operation history data 105 and the index data 106 are stored sequentially.

The user inputs the save command 206 when he or she reaches the desired latest 3DBMD 103. The save command 206 specifies the data recording format. When storing the latest 3DBMD 103 currently processed, in case of storing the current procedural operation history data 105 and the index data 106 together with the primitive 3DBMD 102, the data storing in the format for the index and procedural operation history attached 3DBMD 114 is specified, and alternatively, in case of storing the current procedural operation history data 105, the index data 106 and the primitive 3DBMD 102 as well as the current latest 3DBMD 103, the data storing in the format for the primitive, index and procedural operation history attached 3DBMD 113 is specified.

If necessary, the user specifies the print-out operation for the required image at the printing means (not shown).

The procedural flow is completed after storing the data.

For the 3DBMD without its index data 106 generated after capturing the image, its index data 106 and procedural operation history data 105 can be generated by executing the procedural flow described above.

In case of storing the data in the format for the primitive, index and procedural operation history attached 3DBMD, the stored data can be supplied for the forthcoming operation allowed to start with the latest 3DBMD. As the stored data includes the primitive 3DBMD, by combining the primitive 3DBMD and the procedural operation history data, a series of past operations for generating the latest 3DBMD can be replayed and any state between the primitive 3DBMD and the latest 3DBMB can be recalled as the start point of the user's operation.

In addition, in case of storing the data in the format for the index and procedural operation history attached 3DBMD, as only the primitive 3DBMD, the index data and the procedural operation history data are recorded, the volume of the stored data can be reduced.

Figure 3:
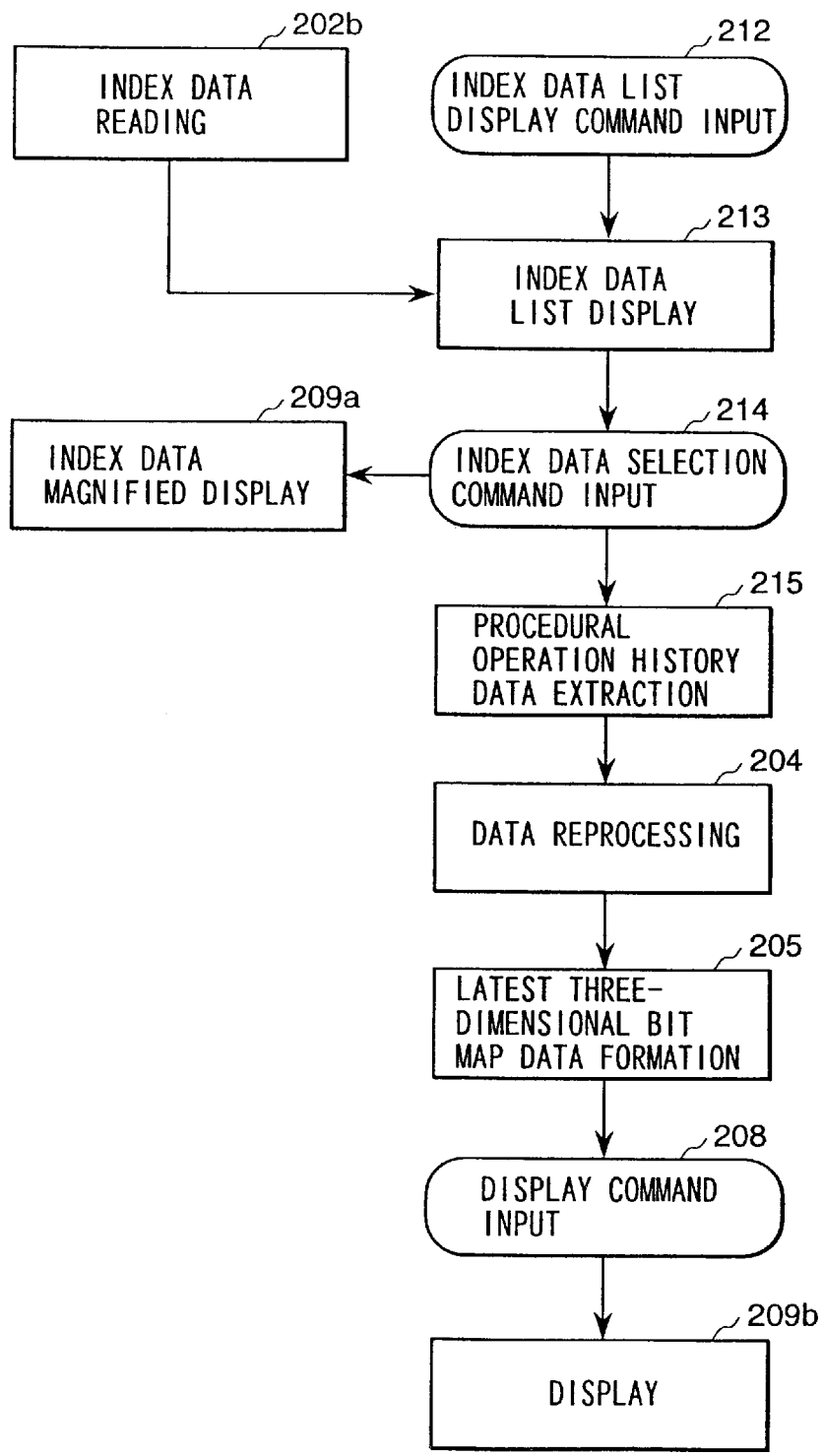
FIG. 3 is a reprocess flowchart.

Next, what is described is the procedural flow performed by the 3DBMD processing system 1*a* for displaying the desired 3DBMD promptly by using the index data 106 of the 3DBMD having the index data 106 and the procedural operation history data 105 (that is, the 3DBMD having a data format for the index and procedural operation history attached 3DBMD 114). This procedural flow is shown in FIG. 3.

At first, the user inputs the index data display command 212 by using the input device 2. In responsive this command, the data processing device 3*a* extracts and reads in the index data 106 from the index and procedural operation history attached 3DBMD recording device 5*c* (Step 202*b*), and displays a list of index data 106 on the display device 4 (step 213).

Next, the user specifies one of the index data 106 corresponding to his or her necessary 3DBMD in the displayed list of index data 106, and inputs the index data selection command 214 from the input device 2. In response to the index data selection command 214, the data processing device 3*a* displays a magnified image of the selected index data 106 on the display device 4 (209*a*) Next, the data processing device 3*a* extracts the procedural operation history data 105 and the primitive 3DBMD 102 corresponding to the extracted index data 106 from the index and procedural operation history attached 3DBMD recording device 5*c* (Step 215). The procedural operation history in the extracted procedural operation history data 105 is applied to the primitive 3DBMD 102 (Step 204). This data to which the procedural operation history corresponds to the latest 3DBMD 103 to be obtained when the extracted index data 106 was generated. The user inputs the display command 208 by using the input device 2, and the data processing device 3*a* display the rendered image of the latest 3DBMD 103 on the display device (Step 209*b*).

According to this embodiment, as the index data does not requires the rendering operation when displaying the index image, it will be appreciated that the data content can be reviewed in, a shorter time of period than displaying the rendered image of the latest 3DBMD for the initial display operation. As plural sets of index data can be displayed all together, it will be appreciated that the time spent for display operation can be made shorter than generating plural rendered images of the latest 3DBMD and displaying them in a single screen. As plural index data are stored, it will be appreciated that plural sets of the latest 3DBMD can be generated from the procedural operation history data and the primitive 3DBMD. As the plural sets of the latest 3DBMD are generated on demand from the procedural operation history data and the primitive 3DBMD, it will be appreciated that the volume of the stored data can be reduced in comparison with the case in which the plural sets of the latest 3DBMD are stored corresponding to the plural sets of index data.

Figure 9:
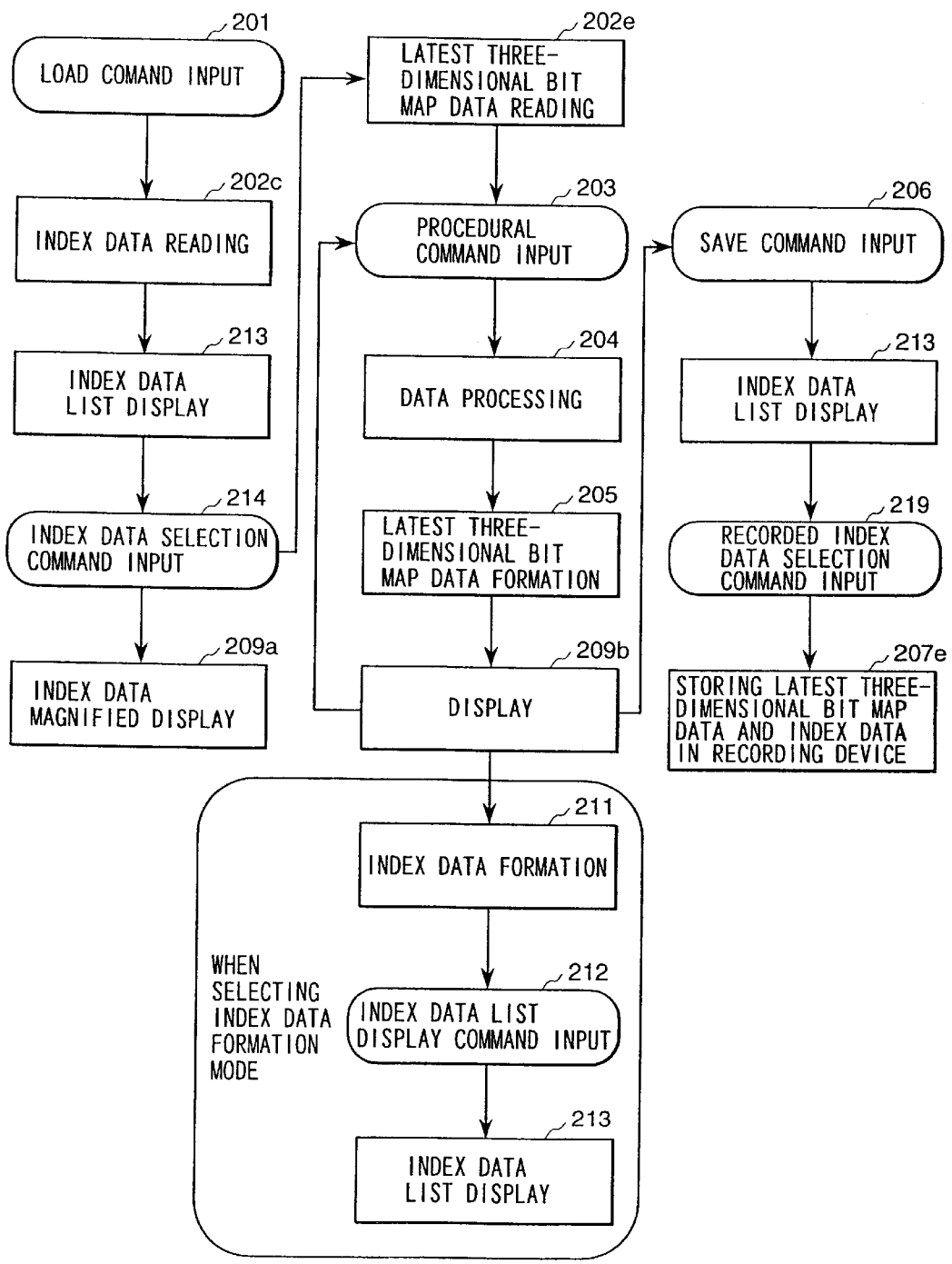
FIG. 9 is a process flowchart.

Next, the procedural flow performed by the 3DBMD processing system 1*a* for editing the 3DBMD having the index data is described. Its procedural flow is shown in FIG. 9. The data format used in this embodiment is a format for the primitive, index and procedural operation history attached 3DBMD. This procedure can be also applied to the data format for the index and procedural operation history attached 3DBMD.

At first, in response to the load command 201 input by the user, the processing system reads in the index data 106 from the primitive data and index attached 3DBMD recording device 5*b* (Step 202*c*), and displays their list (Step 213). Next, the user is required to input the index data selection command 214, and the index data 106 corresponding to the 3DBMD to be edited is selected. It is allowed to display a magnified view of the index data 106 (Step 209*a*). Next, the latest 3DBMD 103 corresponding to the selected index data 106 is read in from the primitive and procedural operation history attached 3DBMD recording device 5*b* (Step 202*e*). In case of editing the index and procedural operation history attached 3DBMD, the latest 3DBMD 103 is generated by selecting the index data 106 at first, and then applying the procedural history specified by the procedural operation history data 105 to the primitive 3DBMD. The subsequent editing procedures are the same as those shown in this embodiment.

Next, in response to the procedural command 203 input by the user, the data processing device 3*a* applies the image processing to the data (Step 204). In this case, the procedural commands 203 includes the operation for data extraction, view point rotation and display mode alteration for density data. And then, the data processing unit 3*a* generates the latest 3DBMD (Step 205) and displays it on the display device 4 (Step 209*b*). The user, viewing this display image, inputs the procedural command again for the further editing operation, and then the procedural flow from the procedural command input 203 to the display 209*a* are repeated. Every time when the display operation 209*a* is performed, the index data 106 is generated and stored in the recording unit.

In case that the user may request to review the course of editing procedures, the user is prompted to input the index data list display command (Step 212), and then the index data list is displayed (Step 213). The recording procedure for the index data 106 under edition can be interrupted by the user setting.

Now that the user can obtain his or her desired latest 3DBMD 103 by repeating the editing procedures described above, the user is prompted to input the save command (206). In response to the user's input of the save command, the data contents initially loaded in the primitive data and procedural operation history attached 3DBMD recording device 5b are updated with the current procedural operation history data 105, the current index data 106 and the current latest 3DBMD. The data (the index attached latest 3DBMD 115) in the user's specified data format including the latest 3DBMD 103 and the index data 106 for the latest 3DBMD 103 is recorded in the index attached latest 3DBMD recording device 5d. In case of suspending the editing procedure, the data is not recorded into the index attached latest 3DBMD recording unit 5d.

Figure 10:
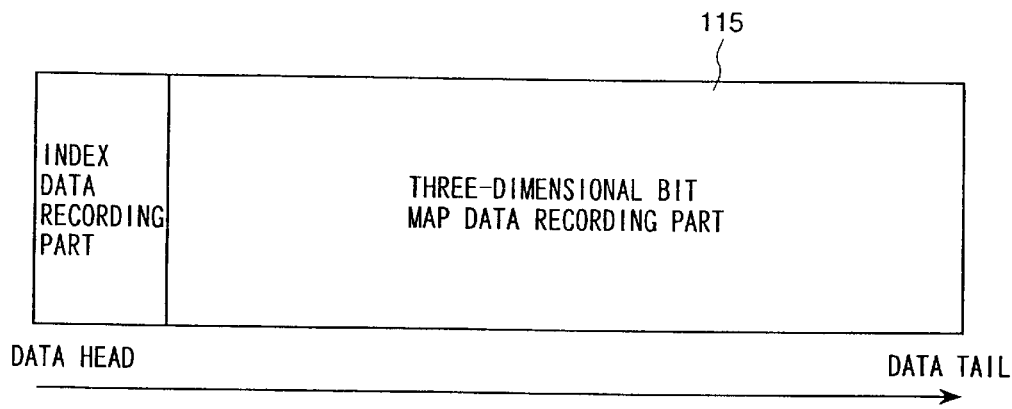
FIG. 10 is an example of three-dimensional bit map data format.
Figure 15:
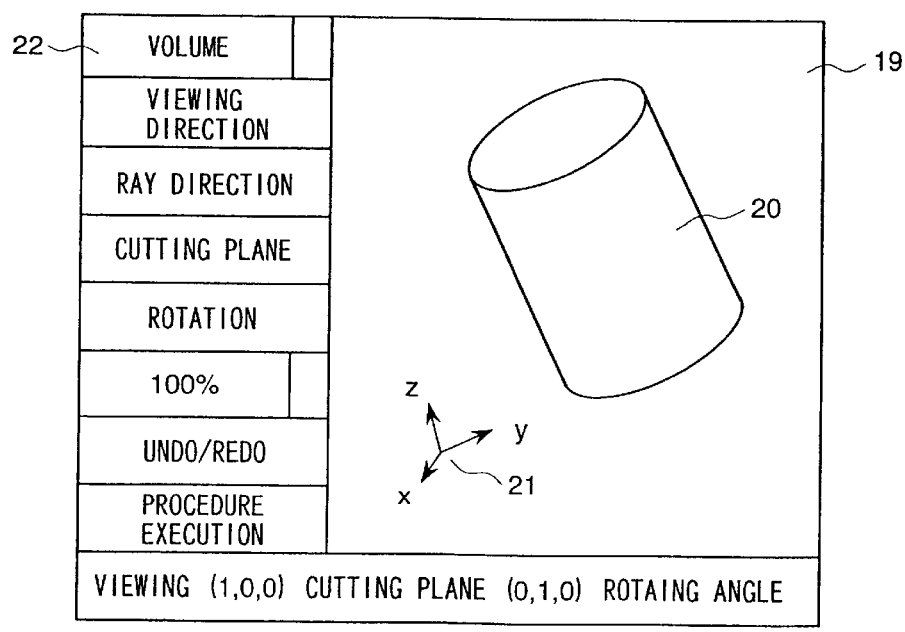
FIG. 15 is an example of scale-down bit map data display and process screen.

FIG. 10 shows a data format for the index attached latest 3DBMD 115. This format has a header for the index data recording part followed by the latest 3DBMD recording part. The index attached latest 3DBMD 115 has an index data part at its header in the data format for storing the data with its editing procedure completed, which allows to review the contents of the 3DBMD without reading directly the latest 3DBMD. This makes it possible for the user to retrieve promptly his or her desired data by viewing a list of index data even if the user has already stored numerous 3DBMD's. In addition, for the data potentially to be unused for the future editing operations, the overall volume of data can be reduced much more than the case in which the primitive 3DBMD's not possible to be used later are stored together.

After the editing operations, the user stores the index attached latest 3DBMD 115 and completes the editing operations.

What described above is a procedural flow in which the user edits the 3DBMD obtained by capturing the image of the object by X-ray CT and obtains his or her desired image.

Now, the display screen of the index data is described next.

Figure 6:
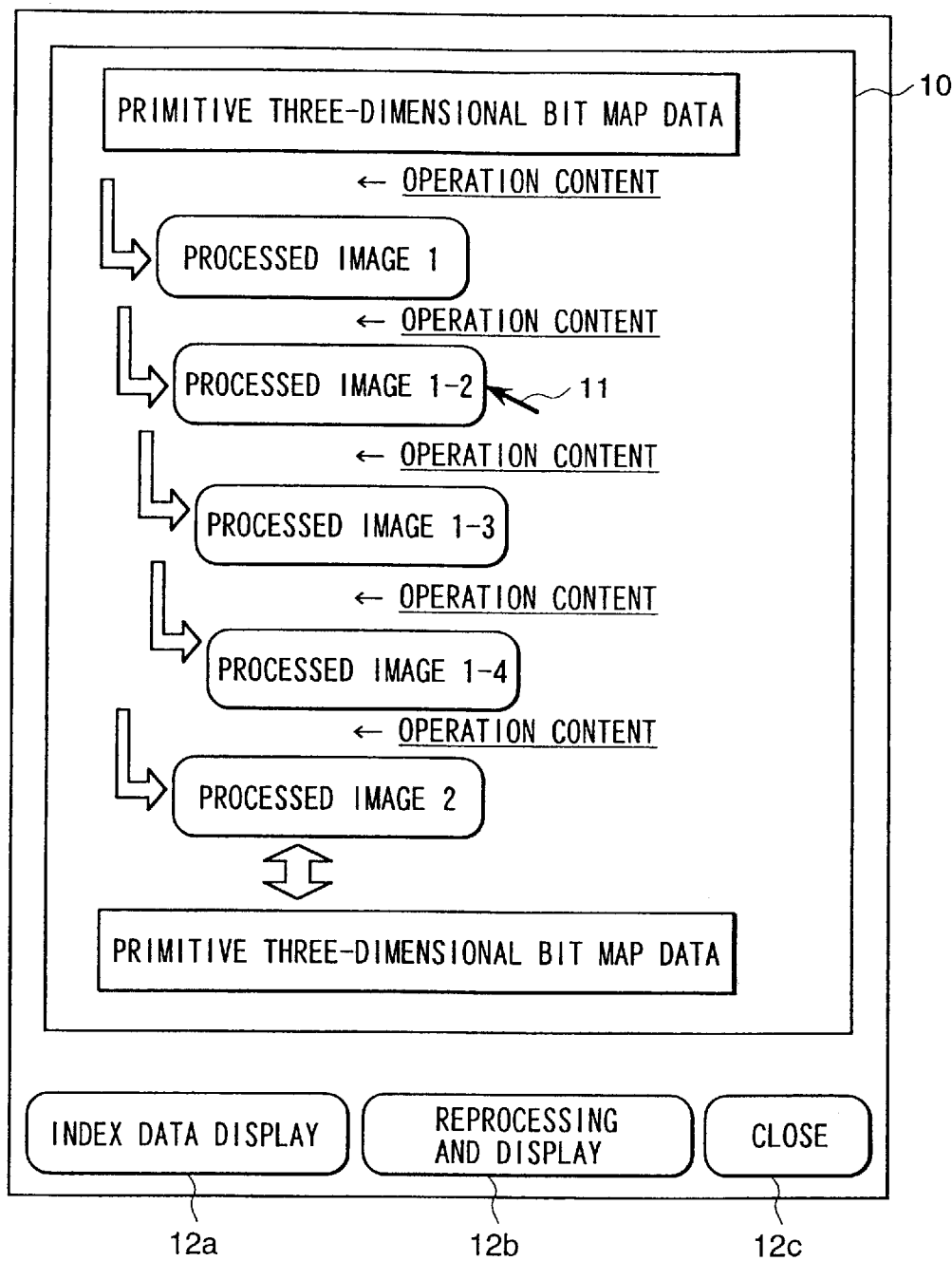
FIG. 6 is an example of index data display and selection screen.

FIG. 6 illustrates a history display screen in case that a list of the index data 106 is displayed in terms of its procedural operation history and operation content. The history display screen 10 presents, hierarchically the individual step of operations and the individual part of decomposed images. The history display screen shows the contents of the operations at the individual steps: for the primitive 3DBMD to the latest 3DBMD. Each of the contents is recorded as the index data 106. The use can select the operation-displayed on the screen by using the pointer 11 with the mouse or the arrow keys of the keyboard. The detail of the operation content and the index data corresponding to the image after applying the designated operation can be displayed by specifying the operation step. The history display screen 10 includes the button 12a for directing the data display command, the button 12b for directing the reprocessing and display command, and the button 12c for closing the screen.

The user may select the operation step and press the reprocessing and display button. In response to this user's action, the data processing unit 3a applies the procedural operation history data 105 covering the procedures up to the selected operation to the primitive 3DBMD, and then displays the rendered image on the screen.

Figure 7:
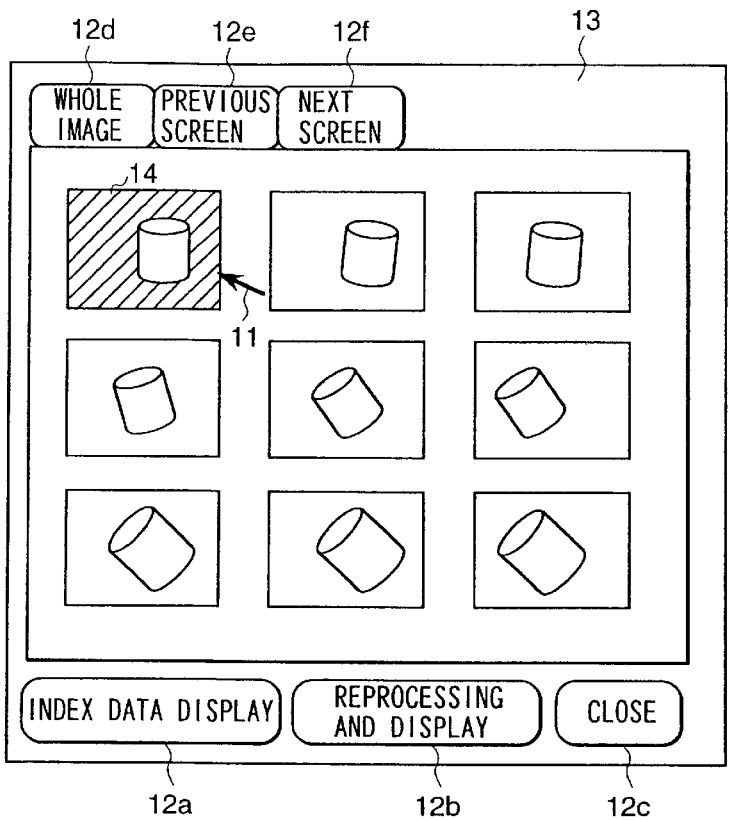
FIG. 7 is an example of index data display and selection screen.

FIG. 7 illustrates a list display screen 13 in case of displaying a list of index data 106 as images. The list display screen 13 displays the images retrieved as the index data obtained after applying the designated operations to the primitive 3DBMD to the latest 3BMD. The user can select the images on the screen by using the pointer 11 with the mouse or the arrow keys of the keyboard. The background color of the selected image 14 is made change so as to be distinguished from others, which makes the user recognize its selection status. The selected image 14 may contain the detail of the corresponding operation content, or its selected and magnified view may be displayed. The list display screen 13 includes the button 12a for directing the index data display command, the button 12b for directing the reprocessing and display command, and the but ton 12c for closing the screen. In case that the selected image can not displayed in a single screen, the user may use the button 12d for requesting to display its whole image in a reduced scale, and the previous-screen button 12e and the next-screen button 12f for scrolling the pages covering the whole image.

The user may select the operation step and press the reprocessing and display button. In response to this user's action, the data processing unit 3a applies the procedural operation history data 105 covering the procedures up to the selected operation to the primitive 3DBMD, and then displays the rendered image on the screen.

Figure 8:
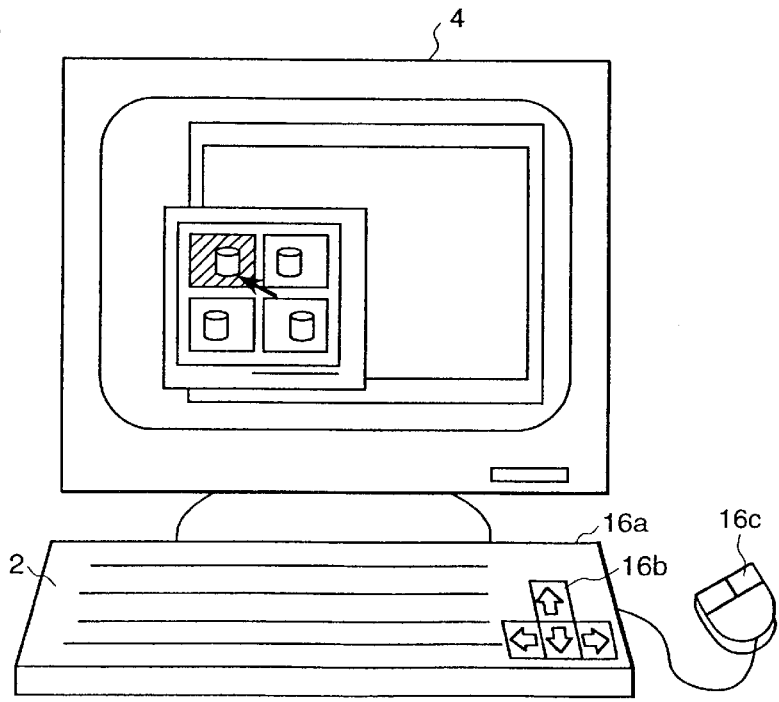
FIG. 8 is an example of user input and display device.

FIG. 8 illustrates the input device 2 and the display device 4. The display device 4 is connected to the input device 2, and the-user viewing the display screen 4 operates the input device. The input device 2 is composed of the keyboard 16a, the arrow keys 16b and the mouse 16c. The keyboard 16a is used for accepting the numerical data input and the command input, the arrow keys 16b are used for specifying the image 14 selected in the images displayed on the screen and the mouse 16c is used for selecting the images and the operations along with the movement of the pointer 11.

According to the above described three-dimensional bit map data processing, by using the 3DBMD having the index data, the time spent for displaying the index data can be made shorter than the time spent for rendering the 3DBMD and displaying the rendered image, and thus the time spent for confirming the content of the 3DBMD can be reduced.

In addition, by storing the history of operations applied to the 3DBMD, a designated steps of operations can be replayed and an arbitrary state backward from the completed 3DBMD can be restored. This means that the undo operation can be applied to the completed 3DBMD.

By storing the 3DBMD before image operations, the 3DBMD after image operations, the procedural operation history data and the index data, the content of the data can be confirmed when restarting the operation. In addition, after confirming the content of the data, the operation for the completed 3DBMD can be restarted. In case of reprocessing the 3DBMD processed before the completed 3DBMD, by applying partially the operations recorded in the procedural operation history data to the completed 3DBMD, the 3DBMD traced backward from the completed 3DBMD can be generated. By applying the image operations to this traced-back 3DBMD, the steps experienced up to the completed 3DBMD can be reattempted.

In this embodiment, the data formats for the primitive, index and procedural operation history 3DBMD, the index and procedural operation history 3DBMD and the index attached latest 3DBMD define the sequence of the index data, the procedural operation history data, the primitive 3DBMD and the latest 3DBMD, which may not be required to be arranged physically and sequentially in the order specified by the data format on the surface of the recording media (for example, the surface of the hard disk in the hard disk recording device) but may be accessed logically in this specified order by the recording device. In addition, even if at least one part of the index data, the procedural operation history data, the primitive 3DBMD and the latest 3DBMD might be recorded physically in a separate recording device, it is allowed to access and readout the designated data logically in this specified order. And furthermore, it is allowed to read out the individual data separately and arrange them in a random access memory so that the data may be ready to be accessible in the random access memory on demand.

The data format for the index attached latest 3DBMD can be used for storing large volume CAD data. Though it is not required to applying the rendering processing to the CAD data for generating its display image, as the large volume CAD data requires an extended period of time for reading in the data and performing complicated topological calculations for generating images, it takes a long period of time to display the images as is the case with the latest 3DBMD. The images can be displayed rapidly by recording the index data at the header of the data contents. In this case, the data format of the index data does not require the topological calculations.

Figure 17:
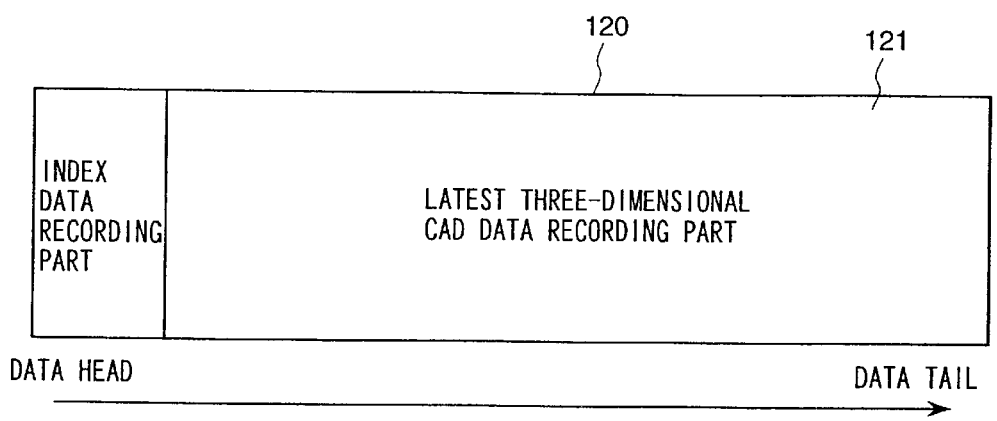
FIG. 17 is an example of CAD data format.

FIG. 17 shows the data format 120 for the index three-dimensional CAD data. The latest three-dimensional CAD data is recorded after the index data 122.

Embodiment 2

This embodiment uses a scale-down 3DBMD in stead of the index data 106 used in the embodiment 1.

At first the sample is scanned by the three-dimensional X-ray CT. The captured data is stored as the primitive 3DBMD in the memory device (a hard disk in this embodiment).

Next, the primitive 3DBMD is made converted into the 3DBMD in this embodiment. FIG. 13 shows an example of the 3DBMD data format having the scale-down 3DBMD in this embodiment.

Figure 13A:
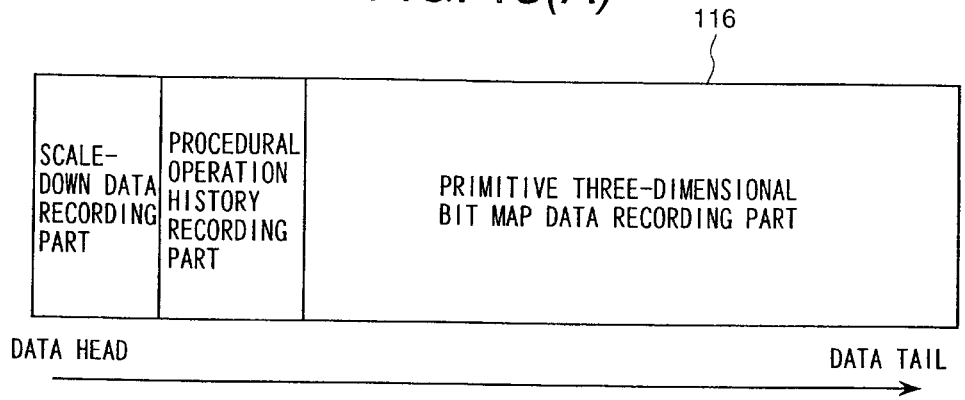
FIG. 13a–c is an example of three-dimensional bit map data format.

The scale-down and procedural operation history attached 3DBMD 115 shown in FIG. 13(A) has a scale-down 3DBMD recording part at the data header followed by a procedural operation history data recording part, and the primitive 3DBMD recording part is recorded at the aftermost part. The scale-down 3DBMD is a reduced data of the 3DBMD obtained by applying the processing directed in the procedural operation history data to the primitive 3DBMD (namely the-reduction of the latest 3DBMD). As the data volume of the scale-down 3DBMD is smaller than the data volume of the 3DBMD, the time spent for reproducing the final display image is short in case of applying the rendering process. Therefore, the time spent for confirming the outline of the latest 3DBMD can be made shorter. As the scale-down 3DBMD is based on the 3DBMD, the operations for rotating and cutting the object can be applied to the data. The time spent for those operations can be extremely shorter than the case in which the same operations are applied to the latest 3DBMD. Therefore, the operations by the users to be applied to the latest 3DBMD may be applied preliminarily to the scale-down 3DBMD and then the outline of the operations' result can be confirmed. Now that the outline of the operations' result is confirmed, the same operations already confirmed can be applied to the latest 3DBMD. In case of applying the image processing to the large amount of data (such as the latest 3DBMD and the primitive 3DBMD), every step of procedures in the overall processing requires a long period of time (which may require the user to wait for ten minutes and a few minutes, which leaves the user on such a halfway as he or she can not leave the seat for expecting the result but he or she have to wait patiently for getting the result), and thus the user have to assume the response time. Therefore, if one step of the processing is held until its prior step of the processing is completed, the overall response time makes extremely long. On the contrary, by means that, after the individual results in the plural steps of the processing are confirmed with their scale-down 3DBMD, the image processing steps recorded in the procedural operation history data and the first-time image processing steps are applied altogether, the user can do other jobs while waiting for the completion of applying the image processing to the primitive 3DBMD. Thus, the processing for the large volume 3DBMD can be performed efficiently. As the 3DBMD before the latest 3DBMD can be generated by using the primitive 3DBMD and the procedural operation history data in the similar manner to the embodiment 1, undo operations can be enabled.

Figure 13B:
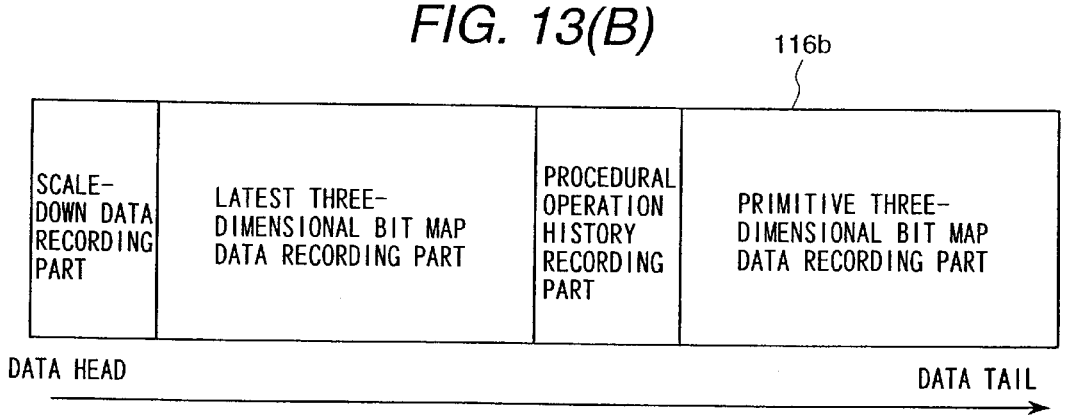

The primitive, scale-down and procedural operation history attached 3DBMD 115 shown in FIG. 13(B) has a data format for recording the primitive 3DBMD together when recording the processed latest 3DBMD. This data format has a scale-down 3DBMD recording part of the latest 3DBMD at the data header followed by the latest 3DBMD recording part, and a procedural operation, history data recording part and a primitive 3DBMD recording part is recorded at the aftermost part. The scale-down 3DBMD is updated every time when the latest 3DBMD is modified. The procedural operation history data records the steps of the processing performed from the primitive 3DBMD to the latest 3DBMD. According to this data- format, the user can confirm the outline of the latest 3DBMD by viewing the scale-down 3DBMD. In case of attempting to regenerate the latest 3DBMD (when undo the past processing applied to the latest 3DBMD), the desired 3DBMD to be obtained by applying the undo operation for the past processing can be generated equivalently by applying the procedural operation history data corresponding to the designated step to the series of past procedures to the primitive 3DBMD by referring to the primitive 3DBMD and the procedural operation history data. In addition, the operations by the users to be applied to the latest 3DBMD may be applied preliminarily to the scale-down 3DBMD and then the outline of the operations result can be confirmed. Therefore, by means that, after the individual results in the plural steps of the processing are confirmed with their scale-down 3DBMD, the first-time image processing steps are applied altogether, the user can do other jobs while waiting for the completion of applying the image processing to the primitive 3DBMD. Thus, the processing for the large volume, 3DBMD can be performed efficiently. As the latest 3DBMD is recorded, a faster processing can be performed rather than the case in which the latest 3DBMD is generated by using the primitive 3DBMD and the procedural operation history data and then the first-time processing is applied to the latest 3DBMD.

Figure 14:
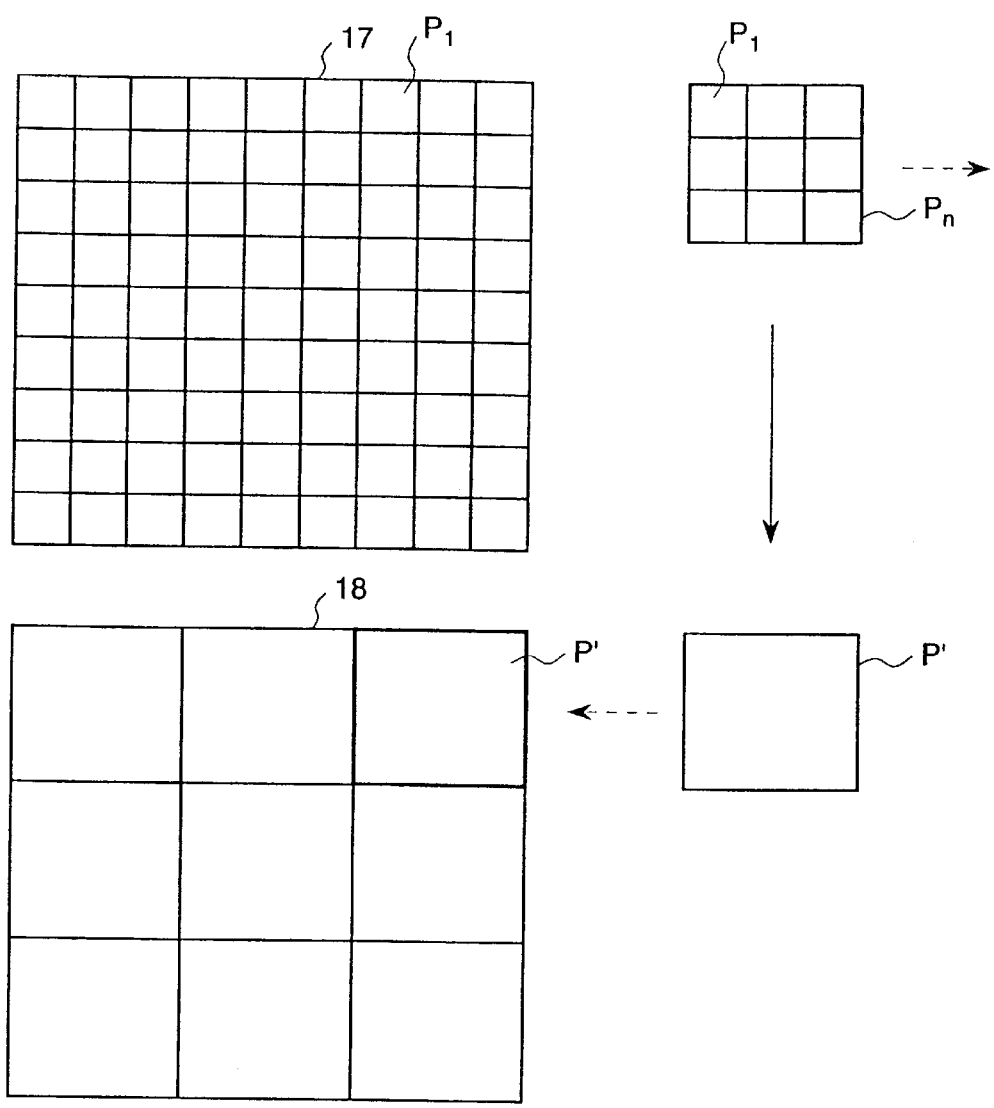
FIG. 14 is an example of generating scale-down bit map data.

By referring to FIG. 14, a method for generating the scale-down 3DBMD from the primitive 3DBMD (or the latest 3DBMD) is described below. For brief explanation, two-dimensional bit map data is used. This method can be applied equivalently to the 3DBMD in principle.

At first, the scale-down factor n is defined. Next, the primitive 3DBMD is loaded, and the size of the scale-down 3DBMD is determined by multiplying the size of the primitive 3DBMD and the inverse number of the scale-down factor n. Next, the pixel groups $P_1$ to $P_n$, each having $\sqrt{n} \times \sqrt{n}$ pixels, in the primitive 3DBMS are considered. Those pixel groups $P_1$ to $P_n$ are degenerated into a single pixel P', and the pixel value (color) V (P') of P' is calculated from the pixel value (color) of the individual pixels in the primitive 3DBMD as follows.

$$V(P')=V(P_1)+V(P_2)+\ldots+V(P_n)/n$$

The above value is calculated for the individual pixel, and the scale-down 3DBMD 18 is generated. In this embodiment, this calculation is performed by the data processing device in response to the command directed by the user.

The large volume 3DBMD captured by the X-ray CT is converted into the scale-down 3DBMD by this method, and the scale-down 3DBMD is appended at the top of the large volume 3DBMD. At this step, the procedural operation history in the scale-down and procedural operation history attached 3DBMD 116 is initialized to be empty. Thereafter every time when the image processing are performed, the procedural operation history is added to the procedural operation history data. In case that the user prefers the data recording in the format for the primitive, scale-down and procedural operation history attached 3DBMD 116b, the data is recorded in the format for the primitive, scale-down and procedural operation history attached 3DBMD 116b by storing the scale-down and procedural operation history attached 3DBMD 115 with its data sequence reversed together with the processed 3DBMD.

Figure 11:
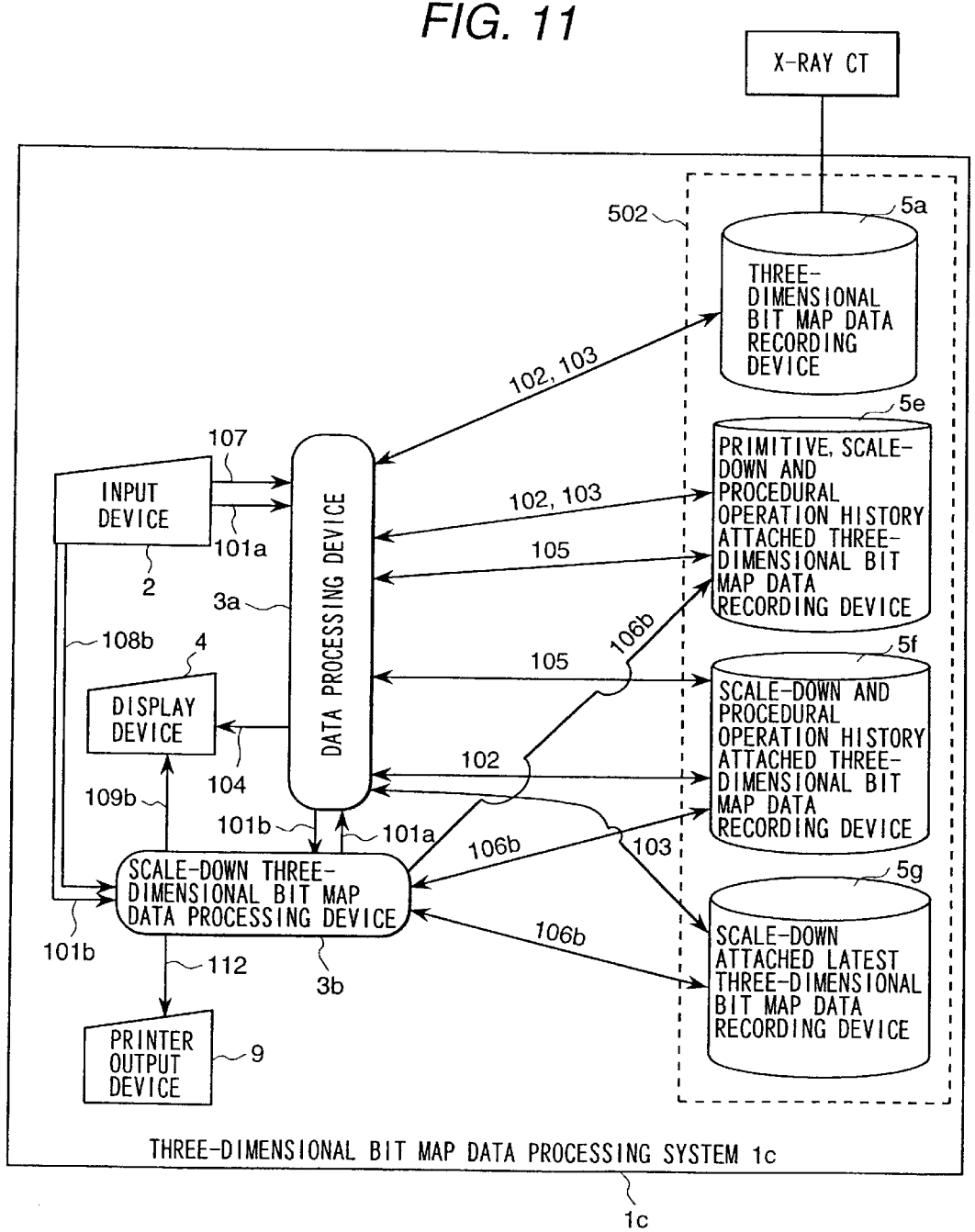
FIG. 11 is a system configuration diagram.

Next, FIG. 11 illustrates a schematic diagram of the structure of the 3DBMD processing system using two formats for the 3DBMD as described above. As the major parts of this system is the same as the embodiment 1, those like parts are not described below.

In this embodiment, the storage device 502 is so configured as to includes individually the 3DBMD recording device 5a, the primitive, scale-down and procedural operation history attached 3DBMD recording device 5e, the scale-down and procedural operation history attached 3DBMD recording device 5f and the scale-down attached latest 3DBMD recording device 5g, but the storage device 502 may be formed alternatively in another configuration as far as recording those elements of data. The electronic computer 503 is so configured as to include individually the data processing device 3a and the scale-down three-dimensional bit map processing device 3b, each corresponding to their specific tasks, which may be formed as a single computer performing those tasks.

The 3DBMD processing system 1c is a system which uses the scale-down 3DBMD instead of the index data 106 in the 3DBMD processing system 1a. The 3DBMD processing system 1c is formed by removing the index data display means 7a and the index data selection means 8 in the 3DBMD processing system 1a and adding the scale-down 3DBMD processing unit 3b for applying the image processing to the scale-down 3DBMD 106 in response to the scale-down 3DBMD processing command 10lb. Its individual recording devices stores the scale-down 3DBMD instead of the index data. Those recording devices include the primitive, scale-down and procedural operation history attached 3DBMD recording device 5e for recording the primitive, scale-down and procedural operation history attached 3DBMD 116b, the scale-down and procedural operation history attached 3DBMD recording device 5f for recording the scale-down and procedural operation- history attached 3DBMD 116, and the scale-down and latest 3DBMD recording device 5g for recording the scale-down and latest 3DBMD 116**c.

Figure 12:
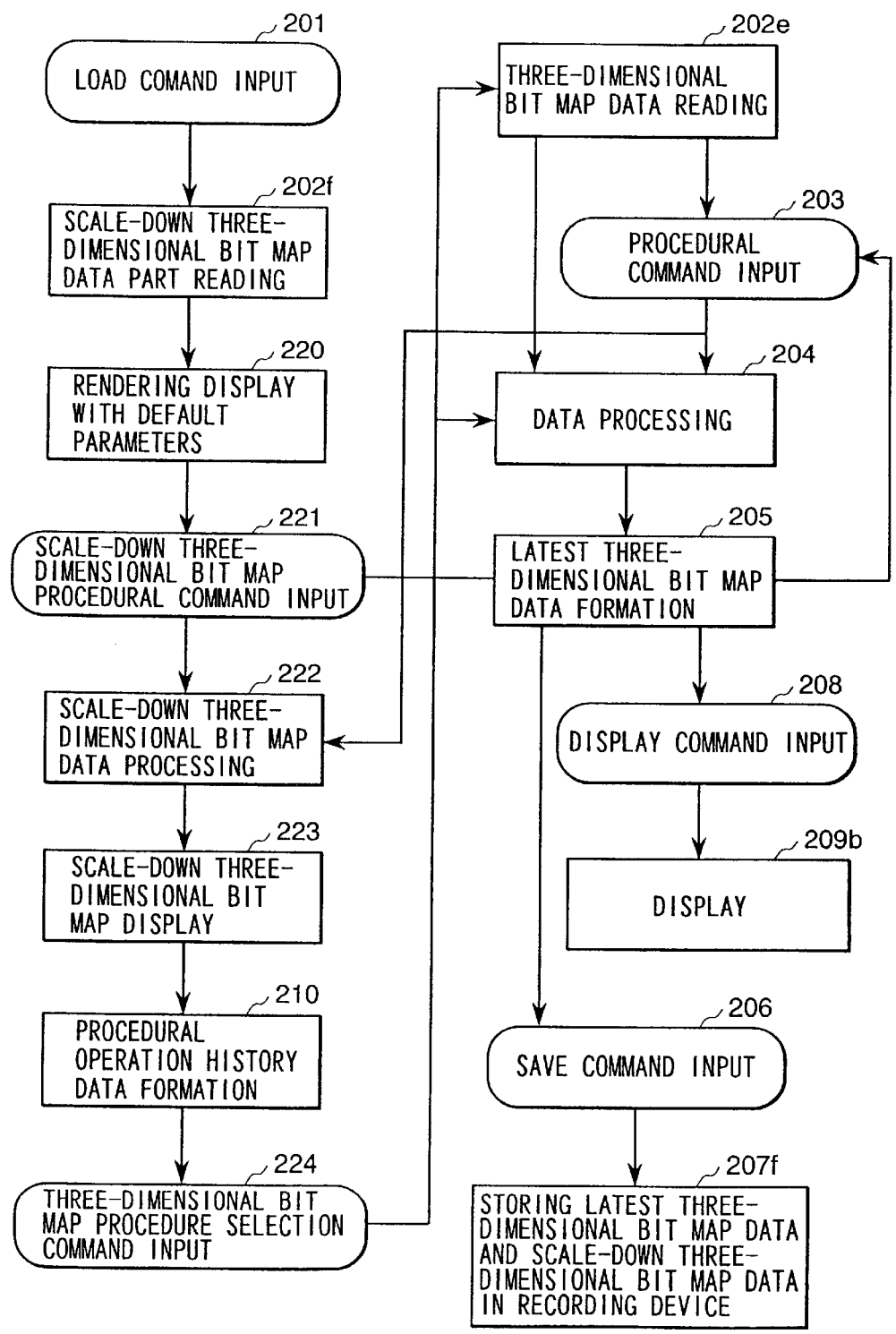
FIG. 12 is a process flowchart.

Next, the procedural flow performed by the 3DBMD processing system 1c for editing the 3DBMD having the scale-down down 3DBMD is described. Its procedural flow is shown in FIG. 12. The data format used in this embodiment is a format for the primitive, scale-down and procedural operation history attached 3DBMD. This procedure can be also applied to the data format for the scale-down and procedural operation history attached 3DBMD.

At first, in response to the load command 201 input by the user, the input device 2 sends the 3DBMD display command 108b to the scale-down 3DBMD processing device 3b. In response this display command, the scale-down 3DBMD processing device 3b reads the scale-down 3DBMD 106b from the primitive, scale-down and procedural operation history attached 3DBMD recording device 5e (Step 202f). The scale-down 3BMD processing unit 3b renders the scale-down 3DBMD 106l in accordance with the default parameters and then sends its result to the scale-down 3DBMD display image data 109b to the display device. The display device displays the scale-down 3DBMD display image data 109b (Step 220). The default parameters are put into the system by the user prior to his or her work for specifying the display format and the visual angle when displaying the scale-down 3DBMD 106b for confirming the data contents, and if the user does not define those parameter values explicitly, the parameters preloaded at the system generation or installation are used.

Next, the scale-down 3DBMD 106 is processed. In response to the procedural command provided by the user, the input device 2 sends the scale-down 3DBMD processing command 101b to the scale-down 3DBMD processing device 3b (Step 221). In response this command, the scale-down 3DBMD processing device 3b applies the image processing to the scale-down 3DBMD 106b (Step 222). This image processing includes rotation, decomposition and partial extraction operations.

Next, the scale-down 3DBMD processing device 3b generates the scale-down 3DBMD display image data 109b for the processed scaled-down 3DBMD 106b and transfers the data to the display device, and the display device displays the data (Step 223). The scale-down 3DBMD display image data 109b generates the procedural operation history data 105 and stores it in the memory (not shown) in the scale-down 3DBMD processing device 3b (or installed outside the scale-down 3DBMD processing device 3b).

As the scale-down 3DBMD is a small-size bit map data, the time spent for processing the scale-down 3DBMD is very short. This data has such a data format advantageous to the user by processing directly the scale-down 3DBMD as the time spent for processing the scale-down 3DBMD is very short while even though the result of the processing the large volume 3DBMD (including the primitive 3DBMD and the latest 3DBMD) can be confirmed briefly.

The user repeats the procedures from the step 221 through the step 210, and then identifies the procedural command providing a designated processing result.

The user, identifying the procedural command for his or her desired processing result (stored in the memory in the scale-down 3DBMD processing device 3b as the procedural operation history data 105), inputs the 3DBMD processing determination command (Step 224). In response to this command, the data processing device 3a reads in the latest, 3DBMD 103 from the primitive, scale-down and procedural operation history attached 3DBMD recording device 5e (Step 202e). In case of using the scale-down and procedural operation history attached 3DBMD 116 as data, the same procedure as processed with the primitive, scale-down and procedural operation history attached 3DBMD 116b may be applied by generating the latest 3DBMD 103 from the primitive 3DBMD 102 and the procedural operation history data 105. The scale-down 3DBMD processing device 5b sends the procedural operation history data 105 stored in the memory to the data processing device 3a as the procedural command 101a.

Next, the data processing device 3a applies the procedural command 101a to the, latest 3DBMD 103 (Step 204) and generates the latest 3DBMD 103 (Step 205). In case of executing plural procedural commands all at once, a given period of time is required. In this case, the user may leave the scene of his or her work and can be involved another job.

Now that the latest 3DBMD 103 is generated, the user inputs the display command 208. In response to the display command 208, the data processing device 3a renders the latest 3DBMD 103 and generates the 3DBMD display image data and sends it to the display device. The display, device displays the 3DBMD display image data and the user confirms the displayed image.

The user, confirming the displayed image, determines whether further image processing is applied again to the scale-down 3DBMD 116b or any image processing is applied directly to the latest 3DBMD 103. In case of processing further the scale-down 3DBMD 106b, the procedural step goes back to the scale-down 3DBMD processing command input 221. In case of processing directly the latest 3DBMD 103, the procedural steps described in the next paragraph are applied. A direct processing of the latest 3DBMD, 103 is used, for example, in case of modifying the resultant error between the latest 3DBMD and the processed scale-down 3DBMD 106b.

At first, the user inputs the procedural command 203. In response to this command, the input device sends the data processing command 101a to the data processing device 3a. The data processing device 3a sends the same procedural request to the scale-down 3DBMD processing device 3b as the scale-down 3DMD processing command 110b. The scale-down 3DBMD processing device 3b applies the scale-down 3DMD processing command 101b to the scale-down 3DBMD 106b, and then displays the scale-down 3DBMD 106b and generates the procedural operation history data 105. At the same time, the data processing device 3a applies the data processing command 101a to the latest 3DBMD 103 (Step 204). In this case, it should be noted that the time spent for processing the scale-down 3DBMD 106b is shorter than the time spent for processing the latest 3DBMD 103. Therefore, the user can review and study primarily the result obtained by processing the scale-down 3DBMD 106b.

Now that the user obtains his or her desired latest 3DBMD 103 at the end of the above procedures, the user inputs the save command 206. At the same time, the user selects the format to be used for storing the data. This format defines the scale-down and procedural operation history attached 3DBMD 115, the primitive, scale-down and procedural operation history attached 3DBMD 115b or the scale-down attached and latest 3DBMD 116c.

Figure 13C:
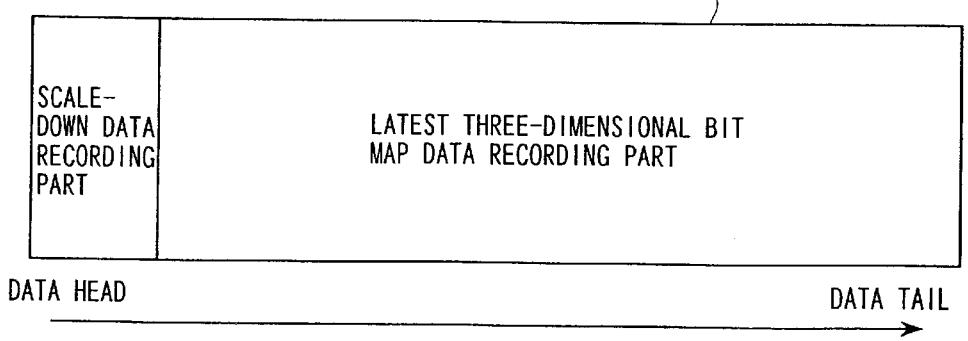

The format for the scale-down attached and latest 3DBMD 116c is described here. As shown in FIG. 13(c), the format for the scale-down attached and latest 3DBMD 116c has the scale-down 3DBMD at its header followed by the latest 3DBMD. The format for the scale-down attached and latest 3DBMD 115c is aimed for storing the data with its editing process completed, which allows the user to understand briefly the contents of the 3DBMD without reading the latest,3DBMD for viewing the data. Therefore, even in case that the user stores a number of 3DBMD, it will be appreciated that the user can retrieve his or her desired data rapidly by browsing a list of displayed scale-down 3DBMD. As the data size of the scale-down 3DBMD is small, the time spent for rendering, if any, might be very short. In addition, as the scale-down 3DBMD has a few possibility to be edited later, its data volume can be reduced much more than the case of recording its data together with the primitive 3DBMD not possible to be edited.

The latest 3DBMD is arranged in the format selected by the user and recorded in the recording device specific to the individual data format. The scale-down attached and latest 3DBMD 115c is recorded in the scale-down attached and latest 3DBMD recording device 5g.

At the end of the above editing procedures, the use stores the data and completes his or her editing work.

What described above is a procedural flow for editing the 3DBMD obtained by capturing the image of the object with X-ray CT in order to provide the output data in the format specified by the user.

Next, the display screen for the scale-down 3DBMD is described. The component 24 [FIG. 1 ] shows a data processing and display screen for the scale-down 3DBMD in this embodiment. The scale-down 3DBMD processing and display screen 19 includes the rendered image 20 of the scale-down 3DBMD, the orientation indicator 21 allowing the user to recognize visually his or her sight direction, and the command selection panel 22, and the user can operates the scale-down 3DBMD by using the mouse, the keyboard and its arrow keys.

Figure 16:
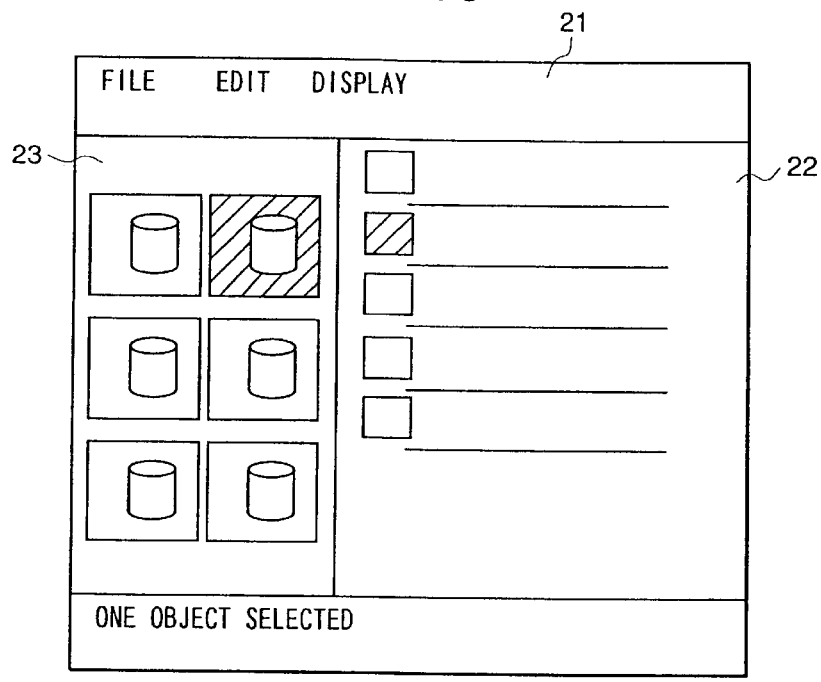
FIG. 16 is an example of operating system file display screen.

FIG. 16 shows a file manager screen. FIG. 16 shows a file manager screen including the area for displaying the outline of the data and the area for displaying a list of file names. A window area 23 is shown at the left side of the screen and shows the image obtained by rendering the scale-down 3DBMD. The window area 22 is also shown for displaying a list of file names. The windows area 23 presents rendered images of the scale-down 3DBMD 106b with their file names specified by the user using a mouse on the window area 22. The user can perform his or her operations in every window area by using a mouse, a keyboard and its arrow keys.

According to this embodiment, the same effect as brought by the embodiment 1 can be attained. In addition, by processing the data having the, scale-down 3DBMD, the same process can be applied to the scale down 3DBMD before processing the latest 3DBMD. As the time spent for processing the scale-down 3DBMD is shorter than the time spent for processing the latest 3DBMD, the outline of the processing result can be confirmed in a shorter period of time than the case of applying the processing directly to the latest 3DBMD.

Embodiment 3

Figure 18:
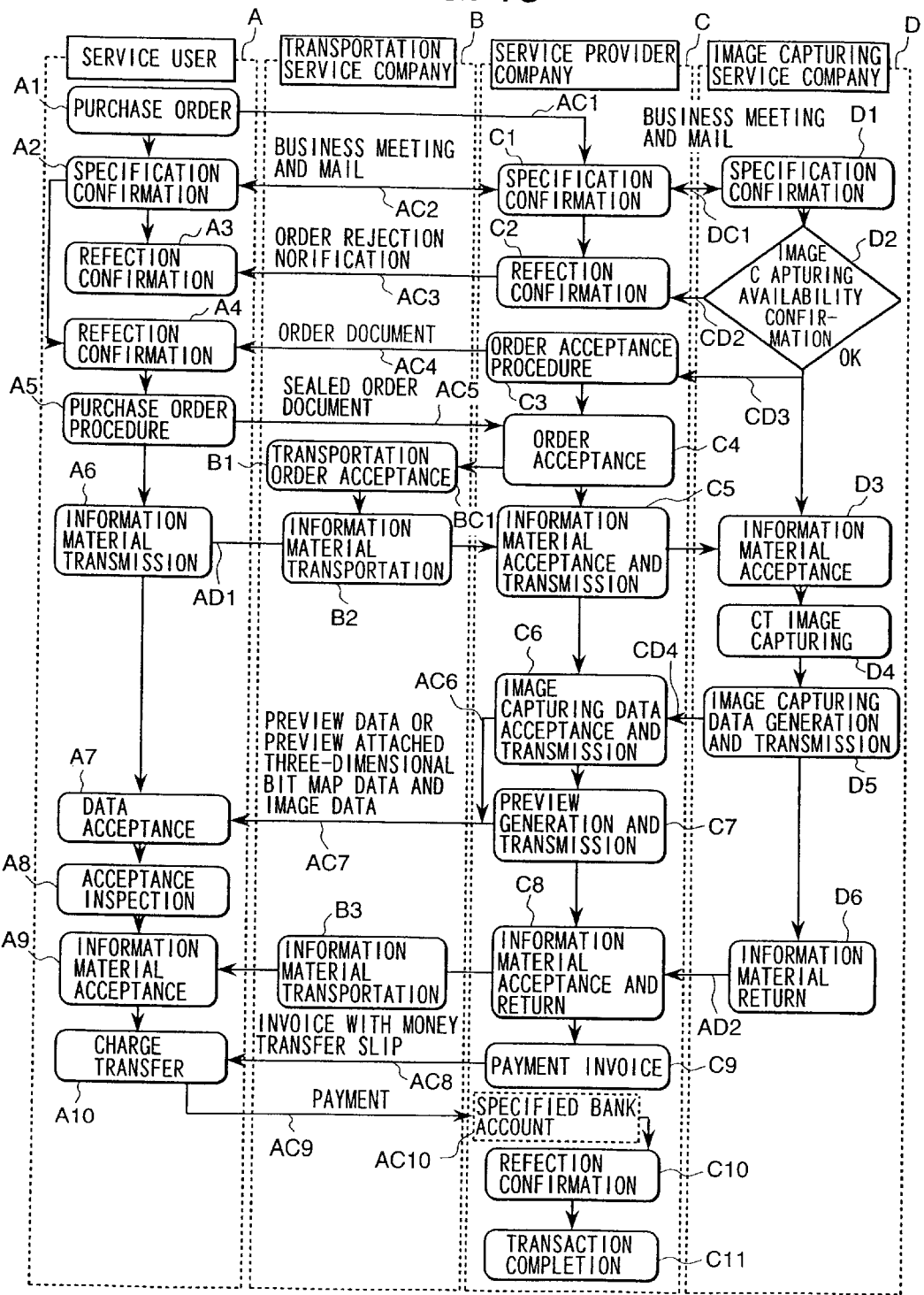
FIG. 18 is a business flow diagram.

Next, a business for providing the 3DBMD by using the 3DBMD described in the embodiments 1 and 2 is described. FIG. 18 shows a procedural flow of the 3DBMD provider service. In this embodiment, the following parties are concerned to one another; a service user A receiving the 3DBMD (generally, a corporate user), a service provider company C providing the 3DBMD, a transportation service company B delivering the target object from the service user A to the service provider company C, and an image capturing service company D (generally, operated by the service provider company C as its subsidiary business) capturing the image of the target object by using the X-ray CT apparatus. Their business flow is described below.

The service user A commits the service purchase order A1, and after transferring the order AC1 to the service provider company C, the service user A completes the specification confirmation A2 by exchanging information at the business meeting or mails AC2 (a mail means either of an e-mail or a postal mail) with the service provider company C. The service provider company C completes the specification confirmations C1 and D1 by exchanging information at the business meeting or mails CD1 about the specification AC1 with the image capturing service company D. After completing the specification confirmation D1, the image capturing service company D judges (at D2) whether the image capturing with the confirmed specification is possible or not, and if the image capturing will not be scheduled, the image capturing rejection notification CD2 is sent to the service provider company C. The service provider company C, receiving the image capturing rejection notification CD2, sends the order rejection notification AC3 to the service user A, and the overall flow is completed when the service user A confirms (A3) the order rejection notification AC3.

In case that the image capturing service company D sends the image capturing acceptance notification CD3 to the service provider company C, the service provider company C commits the order acceptance procedure C3, and sends the order document AC4 to the service user A. In this case, the order acceptance procedure C3 is a procedure for notifying the service provider A the fact that the purchase order is acceptable.

After confirming (A4) the order document AC4, the service user A commits the purchase order procedure A5. The service user fills out the order document at the purchase order procedure A5. Next, the service user A returns the order document to the service provider company C (AC5). The service provider company C, receiving the order document, commits the order acceptance and the image capturing arrangement C4. At this point, the service provider company C commits the request BC1 to the transportation service company B for picking up the target object at the service user A.

After completing the reception B1, the transportation service company B transports the target object from the service user A (AD1 and B2) to the service provider company B. The service provider company C receives the target object, and then transfer the target object to the image capturing service company D (C5). The image capturing service company D receives the target object (D3), and commits the CT image capturing D4 in accordance with the specification. The captured image data is generated by the image capturing (D5), and the captured image data is sent to the service provider company C (D5, CD4). The service provider company C receives the captured image data (C6), and generates (C7) the preview data (the index data 106 or the scale-down 3DBMD 106b) with the method show in the embodiment 1 or 2. The preview data attached 3DBMD and the captured image data are sent to the service user A (AC7). The service user A receives the data (A7) and commits the acceptance inspection (A8).

At this point, the data volume of the captured image data, the latest 3DBMD and the primitive 3DBMD is very large. Therefore, instead of transferring the preview data attached 3DBMD and the captured image data to the service user A, only the preview data may be sent to the service user A first of all. As the service user A can understand the outline of the latest 3DBMD from the preview data, if further editions to be applied to the latest 3DBMD are required, the service user A sends his or her request to the service provider company and then the service provider sends the latest 3DBMD with necessary editions applied to the service user A.

If the preview data is the scale-down 3DBMD 106b, the service user A can recognize the necessary processes to be applied to the primitive 3DBMD by processing the scale-down 3DBMD 106b. The service user A sends its processing contents to the service provider C, and the service provider C applies this processing to the primitive 3DBMD 102. Finally, the service provider sends its result as the preview data attached 3DBMD to the service user A.

According to the above procedures, the volume of the data to be sent from the volume of data sent from the service provider to the service user after capturing the image can be reduced. Owing to this, it will be appreciated that the service provider can provide the service user with his or her desired data more rapidly than the first transmission of the captured image data. In addition, it will be appreciated that the service provider commits the processing to the large volume of 3DBMD all at once. Therefore, even in case that the service user does not have a system for processing the large volume of 3DBMD, the service user can get the resultant data, :obtained by processing the large volume of 3DBMD.

The image capturing service company D returns the target object to the service provider company C after completing the image capturing (D6). The service provider company C carries the target object back to the service user through the transportation service company B (C8, B3). The service provider company C, completing the shipment of the target object to the service user A, sends the invoice with money transfer slip for the payment invoice C9 to the service user A (AC8).

The service user A, receiving the captured image data (A7) and receiving the returned target object (A9), receives the invoice with money transfer slip and then commits the charge transfer A10 to the specified bank account AC10 (C11).

Embodiment 4

Figure 19:
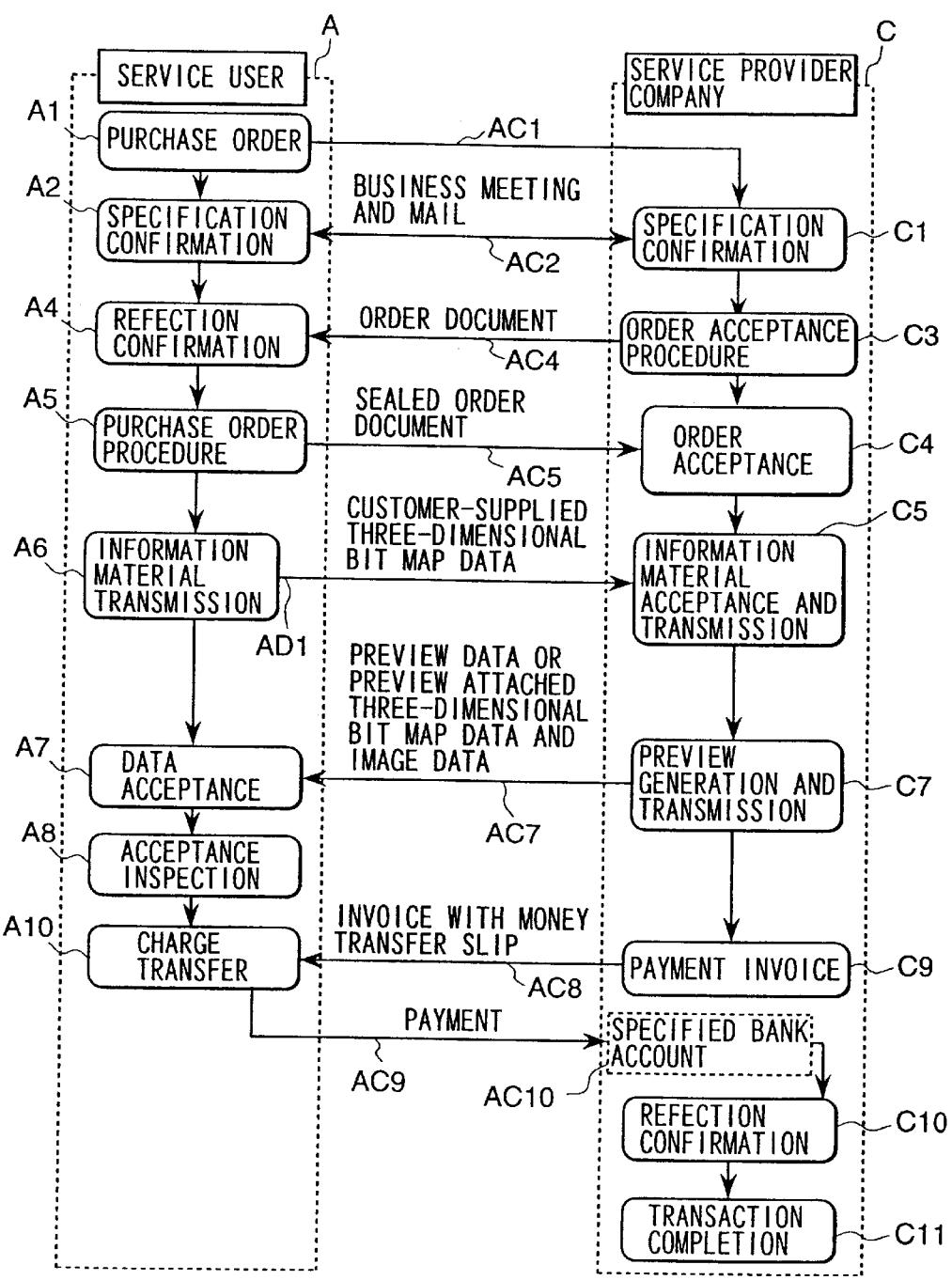
FIG. 19 is a business flow diagram.

Next, a business for providing the process for the 3DBMD by using the 3DBMD described in the embodiments 1 and 2 is described. FIG. 19 shows a procedural flow of the 3DBMD provider service in this embodiment. What will be described are the individual business flows by the service user A (generally, a corporate user) holding the original data of the 3DBMD and asking its image processing and the service provider company C providing the image processing to the 3DBMD.

The service user A commits the service purchase-order A1. After transferring this order AC1 to the service provider company C, the service user completes the specification confirmation A2 by exchanging information at the business meeting or mails AC2 with the service provider company C. The service provider company, receiving the order document AC4, identifies the order (A4) and commits the purchase order (A5). Then, the order document AC5 is returned to the service provider company C, and at the same time, the original data ( 3DBMD) AC11 is forwarded (A6). Receiving the preview data or the preview attached 3DBMD AC7 (A7), the service user commits the acceptance inspection A8 and transfers the payment AC9 to the specified bank account AC10 in response to the invoice with money transfer slip AC8 from the service provider company C, and finally all the transactions are completed.

Next, a business flow by the service provider company C is described. The service provider, receiving the order AC1 from the service user A, commits the order confirmation (C1) by exchanging information at the business meeting or mails (AC), and then commits the order acceptance procedure C3. The service provider company sends the order document AC4 to the service user A, and commits the order acceptance C4 in responsive to the returned order document AC5. The service provider company, receiving the original data (3DBMD) from the: service user A, makes the preview data (index data 106 or scale-down 3DBMD 106b) of this original data by respecting the specification requirement by the service user A. Next, the preview data or the preview-attached 3DBMD AC7 is retuned to the service user A (C7). As in the embodiment 3, it is allowed to send the preview data to the service user at first and next send the large volume of 3DBMD to the service user after the service user identifies the result of the processing to be applied to the original data. The service user A can predict the result of the processing applied to the original data to some extent, but he or she can not confirms its result completely. In case that the service user A, receiving the preview data, recognizes it to be different from his or her expectation, by means that the service provider C attempts to apply alternative processing to the original data until the desired result can be obtained as in this embodiment, the data volume to be exchanged between the service, user A and the service provider can be reduced much more than the large volume of 3DBMD is exchanged directly between them.

After the service user A confirms the contents of the processed data, the service provider sends the invoice with money transfer slip AC8 and commits the payment invoice C9. Finally, the service provider confirms (C10) that the service user A transfers the payment AC9 to the specified bank account AC10, and then completes the transaction.

According to the above embodiment, in dealing large amount of three-dimensional bit map data such as the primitive 3DBMD and the latest 3DBMD, it will be appreciated that the time spent for processing large amount of bit map data can be reduced by adding the data allowing the service user to identify easily the result of the processing to be applied to the original data.

Fifth Embodiment

The fifth embodiment is an embodiment using the scale-down 3DBMD in addition to the index data 106 of the first embodiment. In the shown embodiment, the primitive 3DBMD is generated by overlying a plurality of two-dimensional image data, such as X-ray CT image data or the like. Then, X-ray CT image data thus generated is stored in a storage device (hard disk).

Next, from the primitive 3DBMD, the index data, the process history data, scale-down 3DBMD data are generated. The index data is generated upon generating the two-dimensional image through rendering process for displaying the primitive 3DBMD. The process history data is generated upon processing into the primitive 3DBMD or the scale-down 3DBMD. The scale-down 3DBMD is generated before or after displaying the primitive 3DBMD. Upon displaying the scale-down 3DBMD, a period is taken depending upon size of data. Therefore, time can be saved by generating the scale-down 3DBMD and displaying the same in advance of displaying the primitive 3DBMD. Accordingly, the scale-down 3DBMD is frequently generated in advance of generation of the index data.

Figure 21:
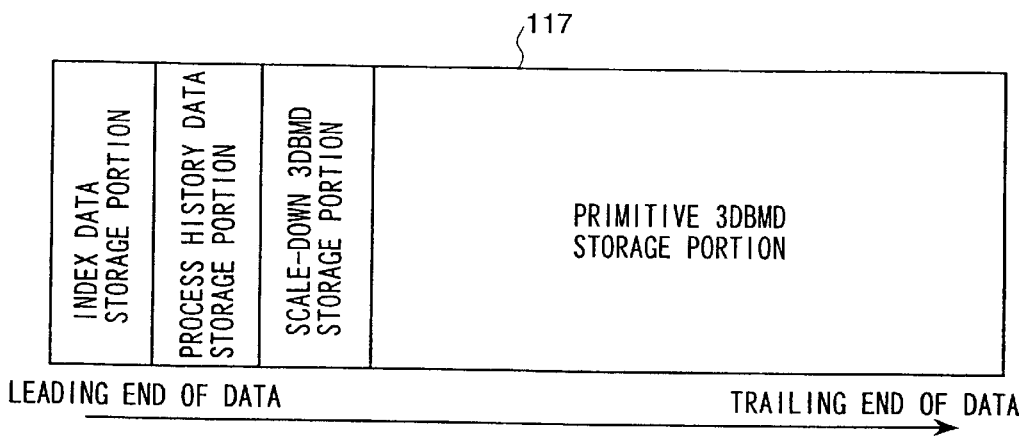
FIG. 21 is a diagrammatic illustration showing a data format.

In the shown embodiment of the data processing apparatus, the index data, the process history data and the scale-down 3DBMD are required to be associated with the primitive 3DBMD. For this reason, while these three data may be stored in separate storage devices, it is preferred that these three data is stored in a single storage device as a single file. FIG. 21 shows an example of a data format of the 3DBMD with the index data, the process history and the scale-down 3DBMD. The shown data has a index data recording portion, a process history recording portion and a scale-down 3DBMD recording portion at the leading end, further has subsequent primitive 3DBMD recording portion. It is possible to record a plurality of index data and scale-down 3DBMD.

The process history data is data storing sufficient information for performing the same process again for all process applied for the primitive 3DBMD. For example, the process history data may be data listing all process conditions as script. Using such data, not only the 3DBMD generated in the midway of the sequentially performed process or the finally generated 3DBMD but also the 3DBMD generated in the midway of the process in trial basis may be generated from the primitive 3DBMD.

The index data: is the two-dimensional image data generated by rendering the primitive 3DBMD or the two-dimensional image data generated by rendering the 3DBMD generated by performing a part of or all of processes described in the process history data with respect to the primitive 3DBMD. While the index data may be whole of or a part of these two-dimensional image data, it is necessary that the 3DBMD corresponding to the index data can be generated utilizing the primitive 3DBMD and the process history data.

Accordingly, when the process history data is not present, the index data becomes only rendering image data of the primitive 3DBMD per se. The case where the process history data is not present, may be the case where the 3DBMD is freshly stored in the storage device as the primitive 3DBMD immediately after generation of the primitive 3DBMD from the X-ray CT image data.

Effect of using of the index data as the rendering image data of the primitive 3DBMD may be quickly selected necessary data from two or more primitive 3DBMD by preliminarily storing only index data. In this case, the process for reading a large data volume primitive 3DBMD (loading to the memory) and the process generating the two-dimensional image data by rendering the primitive 3DBMD and displaying the same can be eliminated, only display process of the index data which can be done in a period one several-hundredth of the period required for the foregoing processes, is required to perform. Furthermore, since the primitive 3DBMD which has large data volume, is not loaded on the memory, the memory can be saved. Thus, even when the memory capacity of the apparatus is small, it becomes possible to display a plurality of data through visual comparison.

Accordingly, when rendering of the primitive 3DBMD having no index data is performed to generate the two-dimensional image data, and when rendering of the new 3DBMD generated by providing certain process for the primitive 3DBMD to generate the two-dimensional image data, these two-dimensional image data may be stored as the index data and then, the corresponding 3DBMD may be erased from the memory.

When the index data corresponds to the result of process described in the process history data, the process described in the process history data may be performed for the 3DBMD by selecting this index data for re-generating the 3DBMD corresponding to the index data. As mode of use, (1) upon the case of selection of data among a plurality of primitive 3DBMD to be loaded and the, process among the processes to be performed, (2) upon selecting data among a plurality of 3DBMD not loaded on the memory, and (3) upon selecting the process among processes described in the process history data in the condition where one primitive 3DBMD is; loaded on the memory.

Figure 22:
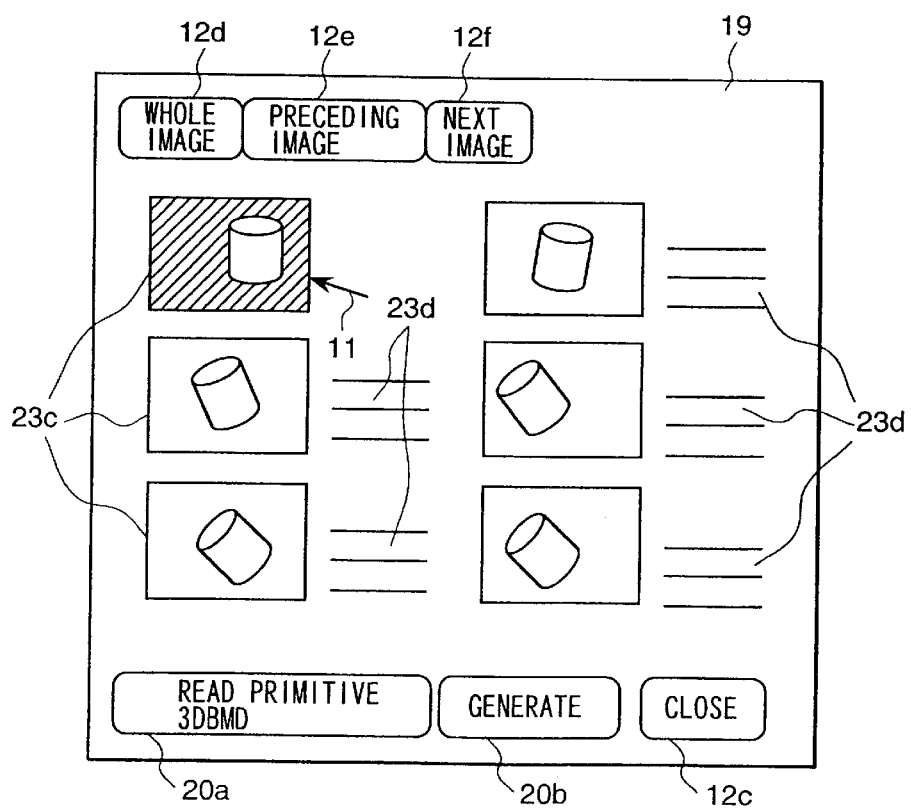
FIG. 22 is an explanatory illustration of a display screen image.

In case of (1), for example, as shown in FIG. 22, the index data of a plurality of primitive 3DBMD are displayed together in a data display window 23c of the display screen 19. On the other hand, the 3DBMD processing system makes reference to the process history data associated with each index data to display the process history information (comment) corresponding to each index data on the right side commend display window 23d of the data display window 23c. Each process history information indicates that the correspondence of each index data to one of the 3DBMD generated by providing one of the processes for the primitive 3DBMD.

Upon displaying the index data and the process history information, since the primitive 3DBMD is not loaded, only index data and the process history data are read without reading the primitive 3DBMD. The index data associated with one primitive 3DBMD is displayed to make association perceptive. For example, it is also possible to display a file name of the primitive 3DBMD corresponding to the comment display window 23d or to display the correspondence between the index data and the primitive 3DBMD in combination in one display screen.

When the index data associated with one primitive 3DBMD is displayed in one display screen, buttons 12e and 12f for page switching, performs function for switching the primitive 3DBMD. In this case, when the button 20a for reading the primitive 3DBMD is depressed, the primitive 3DBMD to be displayed on the display screen can be read. When one 3DBMD is not corresponded to one display screen, it may be possible to read the primitive 3DBMD associated with the index data by depressing the button 20a selecting one of the index data.

On the other hand, upon generation of the 3DBMD, a user may see the index data and process history information, select the index data desired to generate using the pointer 11 and depress the generation button 22b. The 3DBMD processing system is responsive to this operation to perform the process described in the process history data with respect to the primitive 3DBMD to generate the 3DBMD corresponding to the desired index data.

Even in the case of (2), similar image is displayed on the display screen. However, in this case, since only data loading is performed, the generation button 20b is not displayed.

In case of the foregoing (1) and (2), if the index data indicative of the primitive 3DBMD per se is selected, only loading of the primitive 3DBMD is performed. On the other hand, if other index data is selected, a confirmation message may be displayed on the display screen so that generation of new 3DBMD may be performed after acquiring the confirmation of the user.

In case of the foregoing (3), the display screen similar to (1) is displayed. However, in this case, since data has already been loaded, the button for reading the primitive 3DBMD is not displayed.

The scale-down 3DBMD is the 3DBMD scaled down from the primitive 3DBMD setting data volume of data or scale-down magnification at a given value by thinning or other process, and/or the 3DBMD scaled down from the 3DBMD generated by performing a part of or all of the processes of the process history data for the primitive 3DBMD. While the scale-down 3DBMD may be whole or a part of scaled-down 3DBMD, it is required to permit generation of the 3DBMD corresponding to scale-down 3DBMD using the primitive 3DBMD and the process history data. Accordingly, when process history data is not present, the scale-down 3DBMD is the scaled down 3DBMD of the primitive 3DBMD per se.

One effect of using the scale-down 3DBMD of the primitive 3DBMD, is to permit quick selection of necessary data from two or more primitive 3DBMD by preliminarily displaying the scale-down 3DBMD. In this case, process for reading the primitive 3DBMD having large data volume and process for generating and displaying the two-dimensional image data by rendering of the primitive 3DBMD, can be eliminated to require only reading process of the scale-down 3DBMD which can be done in a period one severalth or one several tenth of the period required for reading of the primitive 3DBMD and generating and displaying the two-dimensional image data, and rendering process. Furthermore, since the primitive 3DBMD having large data volume is not loaded on the memory, memory capacity can be saved. Thus, even when the memory capacity of the apparatus is small, it becomes possible to display a plurality of data through visual comparison.

Since the scale-down 3DBMD is a three-dimensional data, display method can be varied by providing process, such as rotation, cutting and so forth. By this, the user may more accurately see the content of the primitive 3DBMD. Accordingly, upon displaying the primitive 3DBMD for which the scale-down 3DBMD is not yet generated, or upon displaying new 3DBMD generated by providing process for the primitive 3DBMD, it may be preferably to requiring confirmation of the user by displaying message on the display screen and to generate and display the scale-down 3DBMD after confirmation by the user.

Another effect of using of the scale-down 3DBMD of the primitive 3DBMD per se, is to permit quick process by providing process for the scale-down 3DBMD in the condition where the primitive 3DBMD is not loaded on the memory or in the condition where no process is provided for the primitive 3DBMD loaded on the memory.

The scale-down, 3DBMD has smaller data volume in comparison with the primitive 3DBMD and requires shorter period for process. Therefore, it become s possible to determine process condition in trial and error basis. For instance, it is possible to perform a plurality of processes for the scale-down 3DBMD with varying the process condition and to perform process for the primitive 3DBMD in the process condition determined from the results. On the other hand, it is also possible to perform different process for the scale-down 3DBMD after process without performing any process for the primitive 3DBMD.

When process is performed for the scale-down 3DBMD, new scale-down 3DBMD is generated for all of the processes to display resultant scale-down 3DBMD on the display screen to permit checking of difference of the results of process depending upon difference of the process conditions. The scale-down 3DBMD resulting from processes in trial and error basis may be updated whenever new processes in trail and error basis is performed. In this case, concerning all processes or all processes except for the processes results of which are not taken in trial and error, the process condition has to record in the process history data. By this, a part or all of the processes performed for the scale-down 3DBMD are finally performed for the primitive 3DBMD to generate the new 3DBMD.

When the scale-down 3DBMD corresponds to the result of the process described in the process history data, the process described in the process history data may be performed for the primitive 3DBMD by selecting the scale-down 3DBMD for generating the 3DBMD corresponding to the scale-down 3DBMD. Different from the index data, the 3DBMD may be one which has not been generated.

As modes of application, there is (1) a case to select data among a plurality of primitive 3DBMD not loaded on the memory for loading and (2) a case to select process among processes described in the process history data in the condition where one primitive 3DBMD is loaded on the memory.

Figure 23:
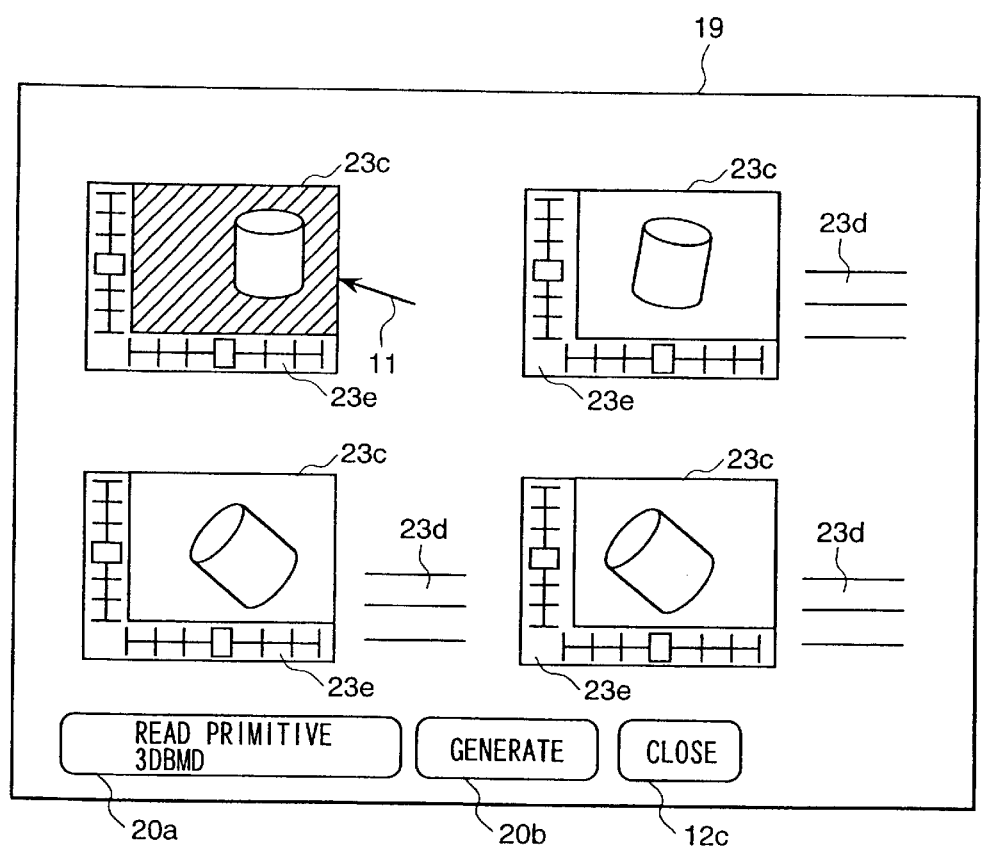
FIG. 23 is an explanatory illustration of the enlarged display screen image

In the case (1), as shown in FIG. 23, for example, the scale-down 3DBMD of, a plurality of primitive 3DBMD Per se are displayed together on the data display window 23c of the display screen 19. In this case, since only data loading is performed, the generation button 20b in FIG. 23 is not displayed. In the comment display window 23d, only data information, such as the file name, data volume and so forth, of the primitive 3DBMD is displayed. The user may watch the scale-down 3DBMD and the data information displayed on the display screen to select the desired scale-down 3DBMD to read the primitive 3DBMD using the pointer 11, and then to depress the button 20a. In this case, the user may vary the display position of the scale-down 3DBMD using a cursor displayed on the position adjusting window 23e. When the button 20a is depressed, the 3DBMD processing system reads in the primitive 3DBMD associated with the selected scale-down 3DBMD.

In the case (2), as shown in FIG. 23, for example, all of the scale-down 3DBMD associated with one primitive 3DBMD are displayed on the data display window 23c. It should be noted that, in this case, since data is already loaded, the button 20a is not displayed. The 3DBMD processing system makes reference to the process history data associated with each scale-down 3DBMD to display the process: history information corresponding to each scale-down 3DBMD on the commend display window 23d. Each process history information indicates the process provided for the primitive 3DBMD with respect to the resultant 3DBMD.

The user may watch the scale-down 3DBMD and the process history information displayed on the display screen to select the scale-down 3DBMD desired to generate using the pointer 11, and depress the generation button 20b. The user may vary the display position of the scale-down 3DBMD using the cursor displayed on the position adjustment window 23e. When the generation button 20b is depressed, the 3DBMD processing system performs process described in the process history data for the primitive 3DBMD to generate the 3DBMD corresponding to the desired 3DBMD. In this case, since it becomes possible to generate the 3DBMD preceding to the latest 3DBMD on the basis of the primitive 3DBMD and the process history data, undo process can be performed.

The individual functions of the process history data, the index data and the scale-down 3DBMD discussed above are similar to those of the first and second embodiment set forth above. In the shown embodiment, all of these functions can be used.

Figure 24:
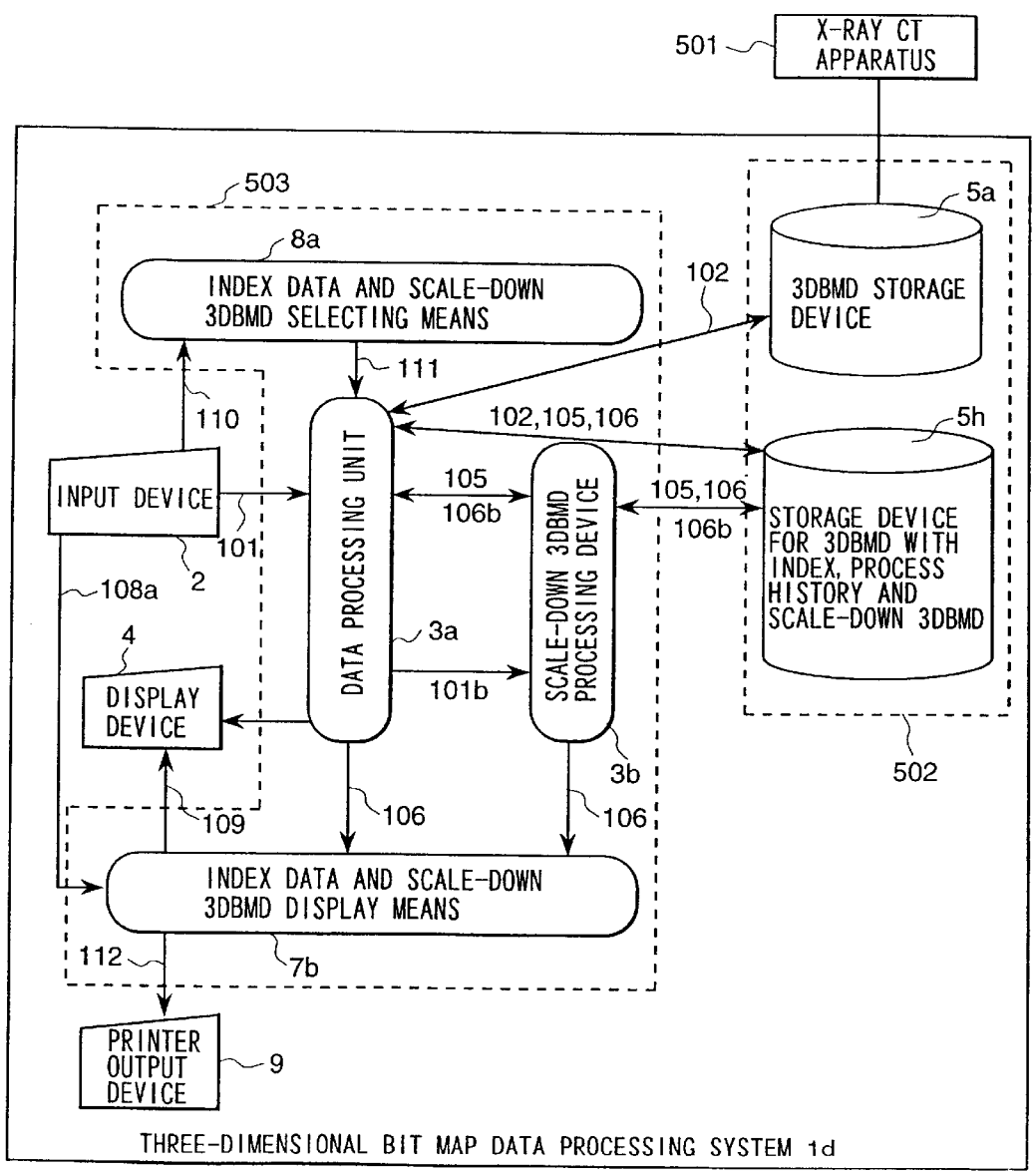
FIG. 24 is a block diagram of the fifth embodiment of the data processing system according to the present invention.

Next, discussion will be given for mode of application unique to the shown embodiment. The mode of application is a method, in which the rendering image of the scale-down 3DBMD is held as the index data. FIG. 24 shows a block diagram showing a construction of the shown embodiment of the 3DBMD processing system. Hereinafter, the 3DBMD processing system will be simply referred to as system. The system 1d handles the scale-down 3DBMD 106b in addition to the index data 106 which is handled by the system 1a. Most part of the shown embodiment of the system is the same as the first embodiment. The common components to those in the first embodiment will be identified by the same reference numerals and detailed discussion for such common components will be eliminated for avoiding redundant disclosure and whereby for keeping the disclosure simple enough to clear understanding of the present invention.

It should be noted that the shown embodiment of the electronic computer 503 is configured to separately have the data processing apparatus 3a, a scale-down 3DBMD processing apparatus 3b, an index data and scale-down 3DBMD selecting means 8a and an index data and scale-down 3DBMD display means 7b adapting to each process contents. However, it is also possible to configure the electronic computer 503 to perform two or more or all of processes with single computer.

The system 1d also includes the scale-down 3DBMD processing apparatus 3b, a storage device 5h for the 3DBMD with index, the process history and scale-down 3DBMD, the index data and scale-down 3DBMD displaying means 7b, the index data and scale-down 3DBMD selection means 8a and so forth as components different from the system 1a. Since the scale-down 3DBMD processing apparatus 3b is the same as system 1c shown FIG. 11, the detailed discussion thereof is eliminated for simplification of disclosure. The storage device 5h for the 3DBMD with index, the process history land scale-down 3DBMD stores the scale-down 3DBMD in addition to the index data and the process history data.

The index data and scale-down 3DBMD displaying means 7b is established by adding a display function of the scale-down 3DBMD to the index data displaying means 7a of the system 1a. The index data and scale-down 3DBMD selecting means 8a is established by addition a selecting function of the scale-down 3DBMD to the index data selecting means 8 of the system 1a. The index data and scale-down 3DBMD displaying means 7b and the index data and scale-down 3DBMD selecting means 8a utilize display function and selecting function as discussed in FIGS. 22 and 23, for example.

Figure 25:
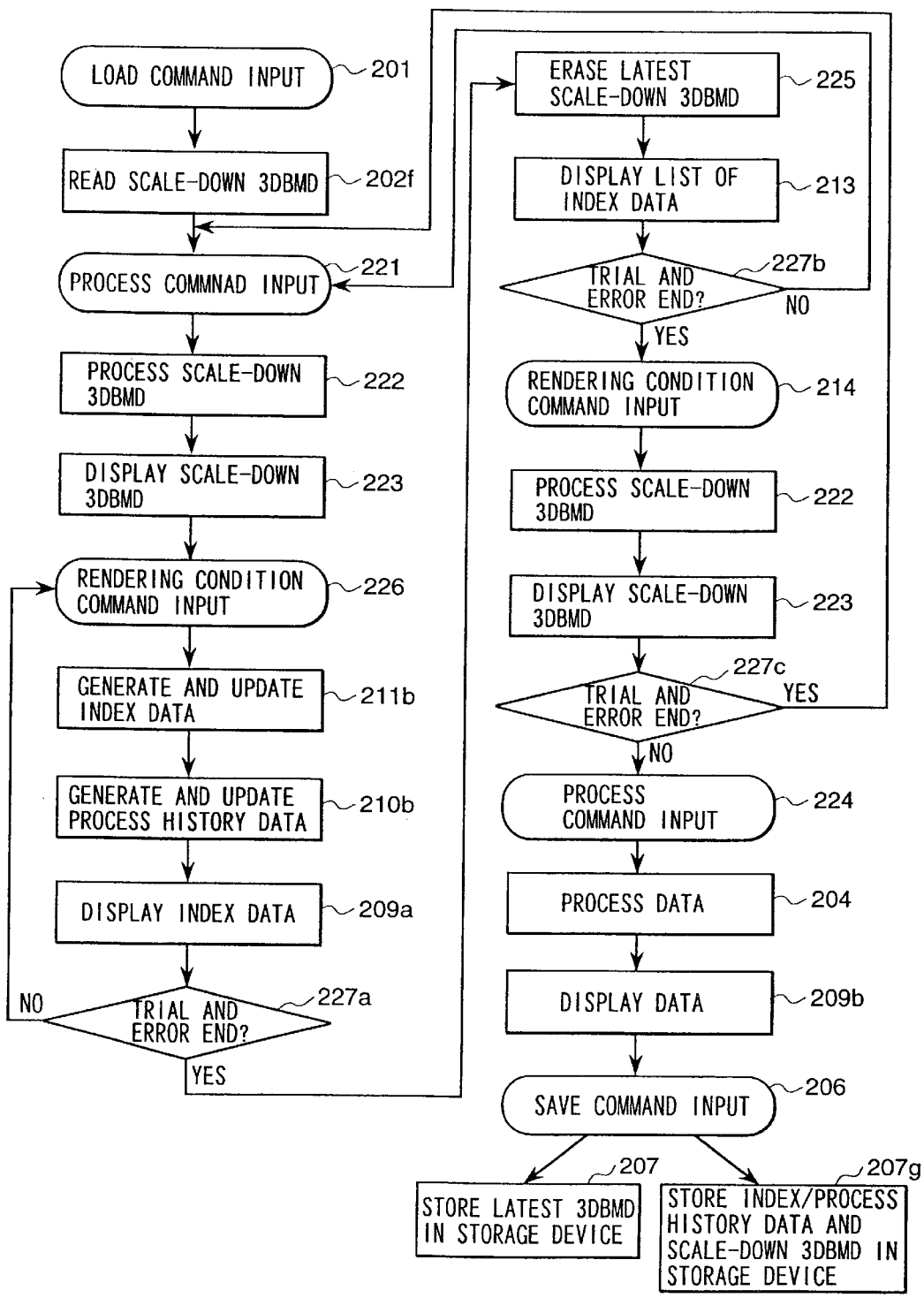
FIG. 25 is a flowchart showing the data processing process.

Next, discussion will be given for a method of editing the 3DBMD having the index data, the process history data and the scale-down 3DBMD by the system 1d with reference to FIG. 25. FIG. 25 is a flowchart showing the shown embodiment of the 3DBMD processing method. Data to be handled in the shown embodiment is the 3DBMD with index, process history and scale-down 3DBMD.

At first, the user inputs a load command with selecting the desired 3DBMD with index, process history and scale-down 3DBMD by the operations discussed with reference to FIGS. 22 and 23 (201). The system 1d does no,t load the primitive 3DBMD and reads out and display the scale-down 3DBMD on the display means (202f). Next, the system id is responsive to the process command input by the user (221) to perform process for the scale-down 3DBMD (222).

This process may be trial and error based process for determining process condition. For this purpose, it becomes necessary to compare a plurality of results of process with respect to a plurality of process conditions. However since the scale-down 3DBMD is 3DBMD, when a large number of data are displayed simultaneously, it may occupy large part of the memory capacity of the apparatus. For adapting to this, in the shown embodiment, when trial and error basis process is performed, the scale-down 3DBMD obtained by processing each process condition, are erased from the memory (225). Instead, the two-dimensional image data generated by rendering the scale-down 3DBMD is displayed in a form of a list as index data (213).

Before erasure of the scale-down 3DBMD, condition for rendering for generating the index data can be varied by displaying the scale-down 3DBMD resulting from the process on the display screen (233), rotating, cutting and so forth. In this case, the system 1d receives the rendering condition command from the user (226), generates the index data and the process history data (211b, 210b), and displays the generated index data by the display means (209a). The system 1d repeats rendering returning to step 226 until reception of input from the user indicative of end of rendering (227a). In response to the input indicative of end of rendering, step 225 is executed.

The index data corresponding to one scale-down 3DBMD may be a plural depending upon different rendering conditions or may be updated (overwritten) every time of varying of the condition (211b). In order to generate such index data, all of the processes initially provided for the scale-down 3DBMD are described in the process history data. When the index data is overwritten, the process history data is also overwritten adapting to the latest index data (210b).

The process done for generating the index data by rendering of the scale-down 3DBMD is not necessary when a plurality of sequential processes are provided for the scale-down 3DBMD or the primitive 3DBMD. However, upon displaying the two-dimensional image data the same as the index data finally, the process history data of the foregoing process may be described.

The system 1d repeats the foregoing process returning to step 221 until reception of input from the user indicative of end of trial and error (227b). Upon reception of the input indicative of end of trial and error, step 214 is executed. The system id receives the selection command of the user with respect to the index data displayed as a result of trial and error (214) and generates the new scale-down 3DBMD from the scale-down 3DBMD before process to display (222, 223). Once the new scale-down 3DBMD is generated[, ]the scale-down 3DBMD before process or a plurality of index data resulting from process on trial and error basis may be erased from the memory.

The system id is responsive to the input from the user indicative of continuing of the process (227c) to return to step 221 to execute the next process. If input indicative of end of process is received, step 224 is executed. The system id receives a selection and process command from the user for the generated index data (224), generates the new 3DBMD providing a series of process for the generated index data (204) to display on the display screen through rendering (209b).

Furthermore, when a save command is received from the user, the system 1d stores the latest scale-down 3DBMD, the index data and process history data heretofore generated in the storage device for storing the 3DBMD with index data, the process history data and scale-down 3DBMD (207g). On the other hand, the new 3DBMD is stored in the storage device for the 3DBMD with index data, the process history data and scale-down 3DBMD or in the storage device for 3DBMD (2107).

With the shown embodiment, after user selects the desired data from the index data displayed in a form of the list, since the scale-down 3DBMD is displayed on the display screen before processing of the primitive 3DBMD, the user may check (preview) in greater detail. Furthermore, the process for the primitive 3DBMD is performed in necessary minimum and in a lump at the end of the process. Therefore, a sequence of processes including setting of condition by trial and error can be done quickly and comfortably using the scale-down 3DBMD and the index data.

It should be noted that, which discussion has been given for the embodiment for erasing the scale-down 3DBMD corresponding to the index data in the shown embodiment, it is also possible not to erase the scale-down 3DBMD corresponding to the index data when the memory has sufficient margin.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be-embodied within a scope encompassed and equivalent thereof with respect to the feature set out in the appended claims.

What claimed is:

1. A data processing apparatus comprising:
   a storage device storing a three-dimensional bit map data and a two-dimensional image data obtained through rendering of said three-dimensional bit map data;
   a data processing unit processing said three-dimensional bit map data stored in said storage device, processing a three-dimensional bit map data after process in said storage device, rendering of said three-dimensional bit map data stores in said storage device, and feeding an obtained two-dimensional image data to a display device; and
   said display device for displaying data fed from said data processing unit.

2. A data processing apparatus as set forth in claim 1, wherein said storage device stores at least a part of process history data relating to history of process provided for said three-dimensional bit map data.

3. A data processing apparatus comprising:
   a storage device for storing a three-dimensional bit map data and a scale-down three-dimensional bit map data generated by compressing said three-dimensional bit map data;
   a data processing unit processing said scale-down three-dimensional bit map data stored in said storage device, processing a scale down three-dimensional bit map data after process in said storage device, and feeding obtained scale-down three-dimensional bit map data after said process to a display device; and
   said display device for displaying data fed from said data processing unit.

4. A data processing apparatus comprising:
   a storage device for storing a three-dimensional bit map data, a scale-down three-dimensional bit map data generated by compressing said three-dimensional bit map data and a two-dimensional image data obtained through rendering of said scale-down three-dimensional bit map data;
   a data processing unit processing said scale-down three-dimensional bit map data stored in said storage device, processing a scale-down three-dimensional bit map data after process in said storage device, rendering of said scale-down three-dimensional bit map data stored in said storage device and feeding obtained two dimensional image data to a display device; and said display device for displaying data fed from said data processing unit.

5. A data processing apparatus as set forth in claim 3, wherein said storage device 'stores at least a part of process history data relating to history of process provided for said scale-down three-dimensional bit map data.

6. A data processing apparatus as set forth in claim 4, wherein said storage device stores at least a part of process history data relating to history of process provided for said scale-down three-dimensional bit map data.

7. A data processing apparatus as set forth in claim 1, wherein a data volume of said three-dimensional bit map data is greater than or equal to 100 Mega bytes and smaller than or equal to 1 Peta byte.

8. A data processing apparatus as set forth in claim 3, wherein a data volume of said three-dimensional bit map data is greater than or equal to 100 Mega bytes and smaller than or equal to 1 Peta byte.

9. A data processing apparatus as set forth in claim 4, wherein a data volume of said three-dimensional bit map data is greater than or equal to 100 Mega bytes and smaller than or equal to 1 Peta byte.

10. A data processing method comprising the steps of:

applying a plurality of processes for a three-dimensional bit map data;

rendering of a plurality of three-dimensional bit map data after process; and displaying at least a plurality of obtained two-dimensional image data together on a display device.

11. A data processing method as set forth in claim 10, which further comprises a step of displaying information relating to history of process applied to said three-dimensional bit map data in association with corresponding said two-dimensional image data.

12. A data processing method comprising the steps of:

deriving a scale-down three-dimensional bit map data by compressing a three-dimensional bit map data;

applying a plurality of processes for said scale-down three-dimensional bit map data; and displaying at least a plurality of scale-down three-dimensional bit map data together on a display device.

13. A data processing method comprising the step of:

deriving a scale-down three-dimensional bit map data by compressing a three-dimensional bit map data;

applying a plurality of processes for said scale-down three-dimensional bit map data;

rendering for a plurality of scale-down three-dimensional bit map data; and displaying at least a plurality of two-dimensional image data together on a display device.

14. A data processing method as set forth in claim 12, which further comprises a step of displaying information relating to a history of process applied to said scale-down three-dimensional bit map data in association with one of corresponding said scale-down three-dimensional bit map data and corresponding said two-dimensional image data.

15. A data processing method comprising the steps of:

acquiring three-dimensional bit map data by picking-up image of a sample by an X-ray CT apparatus on the basis of a demand of client;

generating at least one of a scale-down three-dimensional bit map data by compressing said three-dimensional bit map data, a two-dimensional bit map data by rendering of said three-dimensional bit map data and a two-dimensional bit map data by compressing said three-dimensional bit map data and rendering for same; and transmitting generated data to the client and transmitting said three-dimensional bit map data corresponding to a comment information of the client with respect to the transmitted data.

16. A data processing method comprising the steps of:

receiving at least one of a scale-down three-dimensional bit map data by compressing said three-dimensional bit map data acquired by picking up an image of sample by means of X-ray CT apparatus, a two-dimensional bit map data by rendering of said three-dimensional bit map data and a two-dimensional bit map data by compressing said three-dimensional bit map data and rendering for same from a service provider;

providing a comment information for the received data to said service provider; and receiving said three-dimensional bit map data corresponding to said comment information from said service provider.

* * * * *